(12) United States Patent
Seger et al.

(10) Patent No.: US 9,315,547 B2
(45) Date of Patent: Apr. 19, 2016

(54) NUCLEAR TARGETING SEQUENCES

(71) Applicant: Yeda Research and Development Co. Ltd., Rehovot (IL)

(72) Inventors: Rony Seger, Yavne (IL); Dana Chuderland, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/243,923

(22) Filed: Apr. 3, 2014

(65) Prior Publication Data

US 2014/0212438 A1 Jul. 31, 2014

Related U.S. Application Data

(62) Division of application No. 12/528,465, filed as application No. PCT/IL2008/000249 on Feb. 28, 2008, now Pat. No. 8,748,371.

(60) Provisional application No. 60/903,852, filed on Feb. 28, 2007.

(51) Int. Cl.
| | |
|---|---|
| *A61K 38/00* | (2006.01) |
| *A61K 47/00* | (2006.01) |
| *C07K 7/08* | (2006.01) |
| *C07K 14/47* | (2006.01) |
| *C07K 16/28* | (2006.01) |
| *C07K 16/18* | (2006.01) |
| *C12N 15/113* | (2010.01) |

(52) U.S. Cl.
CPC . *C07K 7/08* (2013.01); *C07K 14/47* (2013.01); *C07K 16/18* (2013.01); *C07K 16/2866* (2013.01); *C12N 15/113* (2013.01); *C07K 2319/09* (2013.01)

(58) Field of Classification Search
CPC .... C07K 14/47; C07K 16/18; C07K 16/2866; C07K 2319/09; C07K 7/08; C12N 15/113
See application file for complete search history.

(56) References Cited

U.S. PATENT DOCUMENTS

| | | | |
|---|---|---|---|
| 6,030,822 A | 2/2000 | Lechner et al. | |
| 6,090,784 A | 7/2000 | Warren | |
| 6,713,606 B1 | 3/2004 | Smith et al. | |
| 2003/0083261 A1 | 5/2003 | Yu et al. | |
| 2004/0091966 A1 | 5/2004 | Zeidler et al. | |
| 2004/0253578 A1 | 12/2004 | Roberts et al. | |
| 2006/0127891 A1 | 6/2006 | McSwiggen et al. | |
| 2010/0099627 A1 | 4/2010 | Seger et al. | |

FOREIGN PATENT DOCUMENTS

| | | | |
|---|---|---|---|
| WO | WO 97/20031 | 6/1997 | |
| WO | WO 98/02454 | 1/1998 | |
| WO | WO 99/04820 | 2/1999 | |
| WO | WO 99/36094 | * 7/1999 | ........... A61K 39/395 |
| WO | WO 00/12114 | 3/2000 | |
| WO | WO 02/051993 | 7/2002 | |
| WO | WO 2008/104979 | 9/2008 | |
| WO | WO 2015/040609 | 3/2015 | |

OTHER PUBLICATIONS

Deeb et al. Identification of an Integrated SV40 T/t-antigen Cancer Signature in Aggressive Human Breast, Prostate, and Lung Carcinomas with Poor Prognosis. Cancer Res Sep. 1, 2007, vol. 67, No. 17, pp. 8065-8080.*
Communication Relating to Results of the European Search Report Dated Jan. 26, 2015 From the European Patent Office Re. Application No. 14185916.5.
Advisory Action Before the Filing of an Appeal Brief Dated Nov. 12, 2013 From the US Patent and Trademark Office Re. U.S. Appl. No. 12/528,465.
International Preliminary Report on Patentability Dated Jul. 29, 2010 From the International Bureau of WIPO Re. Application No. PCT/IL2008/000249.
International Search Report and the Written Opinion Dated Jul. 6, 2010 From the International Searching Authority Re.: Application No. PCT/IL08/00249.
Invitation to Pay Additional Fees Dated Apr. 29, 2010 From the International Searching Authority Re.: Application No. PCT/IL08/00249.
Notice of Allowance Dated Dec. 23, 2013 From the US Patent and Trademark Office Re. U.S. Appl. No. 12/528,465.
Office Action Dated May 7, 2012 From the Israel Patent Office Re. Application No. 200578 and Its Translation Into English.
Office Action Dated Jul. 14, 2011 From the Israel Patent Office Re. Application No. 200578 and Its Translation Into English.
Office Action Dated Dec. 29, 2013 From the Israel Patent Office Re. Application No. 219783 and Its Translation Into English.
Official Action Dated Aug. 6, 2013 From the US Patent and Trademark Office Re. U.S. Appl. No. 12/528,465.
Official Action Dated Sep. 7, 2011 From the US Patent and Trademark Office Re. U.S. Appl. No. 12/528,465.
Official Action Dated Nov. 9, 2011 From the US Patent and Trademark Office Re. U.S. Appl. No. 12/528,465.
Official Action Dated May 15, 2012 From the US Patent and Trademark Office Re. U.S. Appl. No. 12/528,465.
Official Action Dated Mar. 20, 2013 From the US Patent and Trademark Office Re. U.S. Appl. No. 12/528,465.
Official Action Dated Nov. 29, 2011 From the US Patent and Trademark Office Re. U.S. Appl. No. 12/528,465.
Response Dated Oct. 5, 2011 to Official Action of Sep. 7, 2011 From the US Patent and Trademark Office Re. U.S. Appl. No. 12/528,465.
Response Dated Nov. 14, 2011 to Office Action of Jul. 14, 2011 From the Israel Patent Office Re. Application No. 200578.

(Continued)

*Primary Examiner* — Marcela M Cordero Garcia

(57) ABSTRACT

Isolated peptides comprising nuclear targeting activity or being capable of preventing endogenous nuclear targeting activity are disclosed. Polynucleotides encoding same, pharmaceutical compositions comprising same, as well as uses thereof are also disclosed.

5 Claims, 21 Drawing Sheets

(56) References Cited

OTHER PUBLICATIONS

Supplementary European Search Report and the European Search Opinion Dated Feb. 27, 2014 From the European Patent Office Re. Application No. 08710249.7.

Adachi et al. "Two Co-Existing Mechanisms for Nuclear Import of MAP Kinase: Passive Diffusion of a Monomer and Active Transport of a Dimer", The EMBO Journal, 18(19): 5347-5358, 1999.

Boulton et al. "REcName: Full=Mitogen-Activated Protein Kinase 1; Short=MAP Kinase 1; Short:MAPK 1; AltName: Full=ERT1; AltName: Full-"Extracellular Signal-Regulated Kinase 2; Short=ERK-2; AltName: Full=MAP Kinase Isoform P42; Short=P42-MAPK; AltName: Full=Mitogen-Activated Protein Kianse 2; Short=MAPK Kinase 2; Short=MAPK 2, UniProtKB/Swiss-Prot [Online], UniProtKB/Swiss-Prot: P63086.3, GenBank Accession No. P63086, Dec. 11, 2013.

Chen et al. "Nuclear Localization and Regulation of ERK- and RSK-Encoded Protein Kinases", Molecular and Cellular Biology, 12(3): 915-927, Mar. 1992.

Christophe et al. "Nuclear Targeting of Proteins: How Many Different Signals?", Cellular Signalling, 12: 337-341, 2000.

Costa et al. "Dynamic Regulation of ERK2 Nuclear Translocation and Mobility in Living Cells", Journal of Cell Science, 119(23): 4952-4963, 2006.

GenBank "Importin-7 [Homo sapiens]", GenBank Submission, NCBI Reference Sequence: NP_006382.1, Retrieved From the Internet, 3 P., 1997.

Goddard et al. "High Affinity Binding of an N-Terminal Myristoylated P60src Peptide", The Journal of Biological Chemistry, 264(26): 15173-15176, Sep. 15, 1989.

Hoffmann et al. "Separation of Sets of Mono- and Diphosphorylated Peptides by Reversed-Phase High Performance Liquid Chromatography", Analytica Chimica Acta, 352: 327-333, 1997.

Jaaro et al. "Nuclear Translocation of Mitogen-Activated Protein Kinase Kinase (MEK1) in Response to Mitogenic Stimulation", Proc. Natl. Acad. Sci. USA, 94: 3742-3747, Apr. 1997.

Jäkel et al. "Importin Beta, Transportin, RanBP5 and RanBP7 Mediate Nuclear Import of Ribosomal Proteins in Mammalian Cells", The EMBO Journal, 17(15): 4491-4502, 1998.

Joseph et al. "Interaction of Peptides Corresponding to Fatty Acylation Sites in Proteins With Model Membranes", The Journal of Biological Chemistry, 270(28): 16749-16755, Jul. 14, 1995.

Lorenzen et al. "Nuclear Import of Activated D-ERK by DIM-7, an Importin Family Member Encoded by the Gene Moleskin", Development, 128: 1403-1414, 2001. Abstract, p. 1403-1404.

Moroianu "Nuclear Import and Export Pathways", Journal of Cellular Biochemistry Supplements, 32/33: 76-83, 1999.

Muller et al. "TransMabs: Cell-Penetrating Antibodies, the Next Generation", Expert Opinion in Biological Therapy, 5(2): 1-5, 2005. Abstract, p. 2, § 6.

Owaki et al. Extracellular Signal-Regulated Kinases in T Clees: Characterization of Human ERK1 and ERK2 cDNAs, Biochemical and Biophysical Research Communication, 182(3): 1416-1422, Feb. 14, 1992.

Rubinfeld et al. "Identification of a Cytoplasmic-Retention Sequence in ERK2", The Journal of Biological Chemistry, XP002981241, 274(43): 30349-30352, Oct. 22, 1999. Abstract.

Sparrow et al. "Chemical Synthesis and Biochemical Properties of Peptide Fragments of Apolipoprotein-Alanine", Proc. Natl. Acad. Sci. ISA, PNAS, 70(7): 2124-2128, Jul. 1973.

Walter et al. "Antibodies Specific for the Carboxy- and Amino-Terminal Regions of Simian Virus 40 Large Tumor Antigen", Proc. Natl. Acad. Sci. USA, 77(9): 5197-5200, Sep. 1980.

Wu et al. "Drug Targeting of a Peptide Radiopharmaceutical Through the Primate Blood-Brain Barrier In Vivo With a Monoclonal Insulin Receptor", Journal of Clinical Investigation, 100(7): 1804-1812, Oct. 1997.

Xu et al. "Distinct Domain Utilization by Smad3 and Smad4 for Nucleoporin Interaction and Nuclear Import", The Journal of Biological Chemistry, 278(43): 42569-42577, Oct. 24, 2003.

Yao et al. "Non-Regulated and Stimulated Mechanisms Cooperate in the Nuclear Accumulation of MEK1", Oncogene, 20(52):7588-7596, 2001.

Yazicioglu et al. "Mutations in ERK2 Binding Sites Affect Nuclear Entry", The Journal of Biological Chemistry, 282(39): 28759-28767, Sep. 28, 2007.

Examiner-Initiated Interview Summary Dated May 12, 2014 From the US Patent and Trademark Office Re. U.S. Appl. No. 12/528,465.

Office Action Dated Oct. 29, 2014 From the Israel Patent Office Re. Application No. 219783 and Its Translation Into English.

International Search Report and the Written Opinion Dated Dec. 17, 2014 From the International Searching Authority Re. Application No. PCT/IL2014/050822.

* cited by examiner

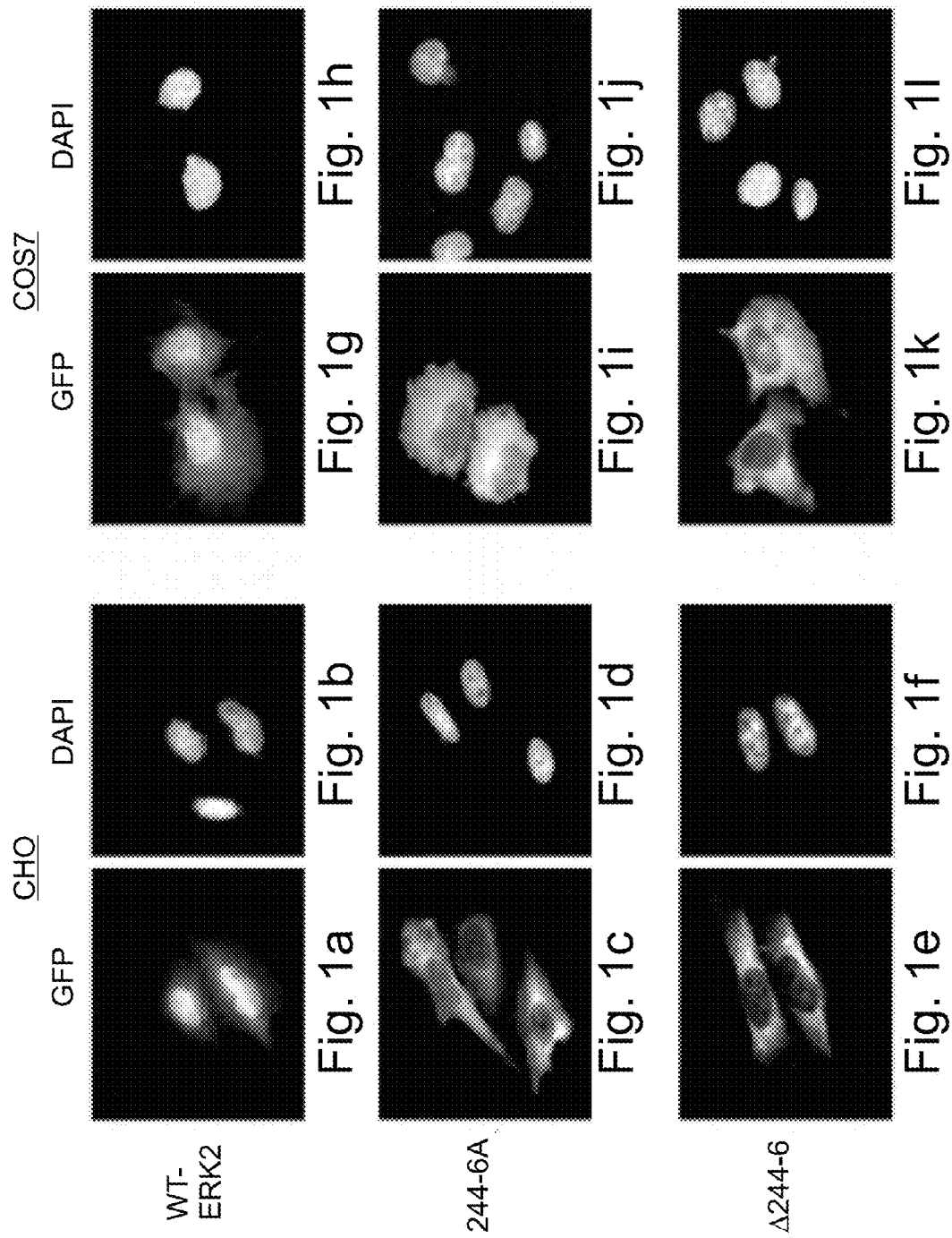

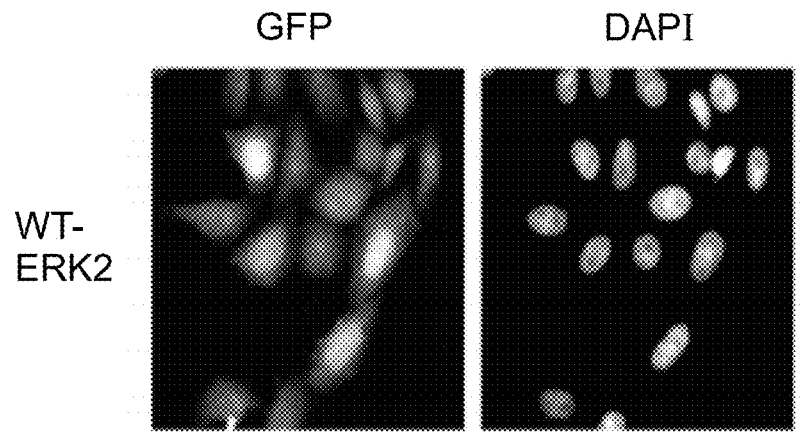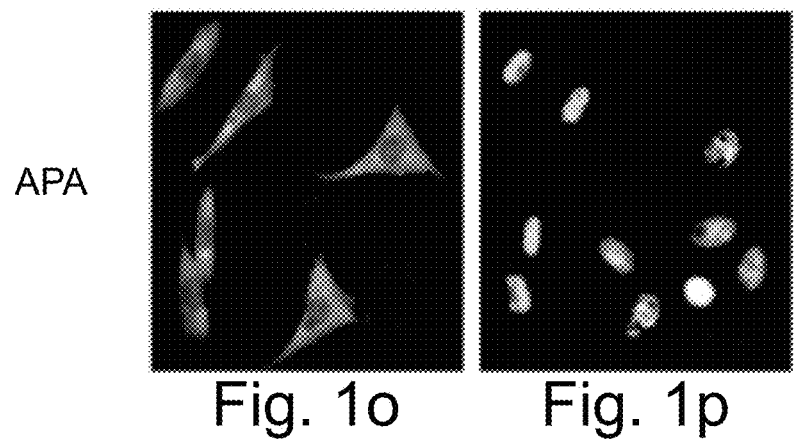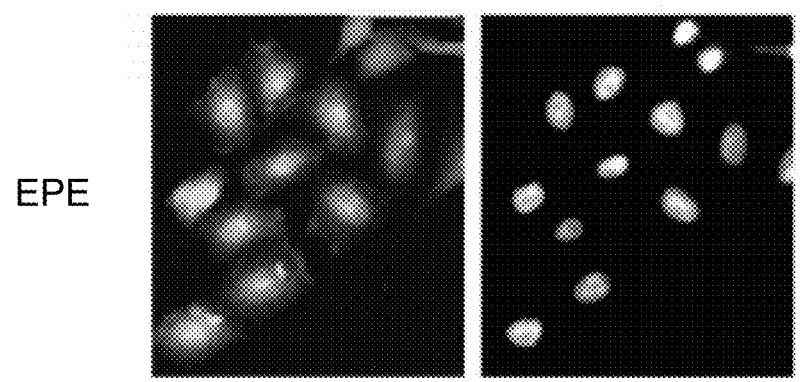

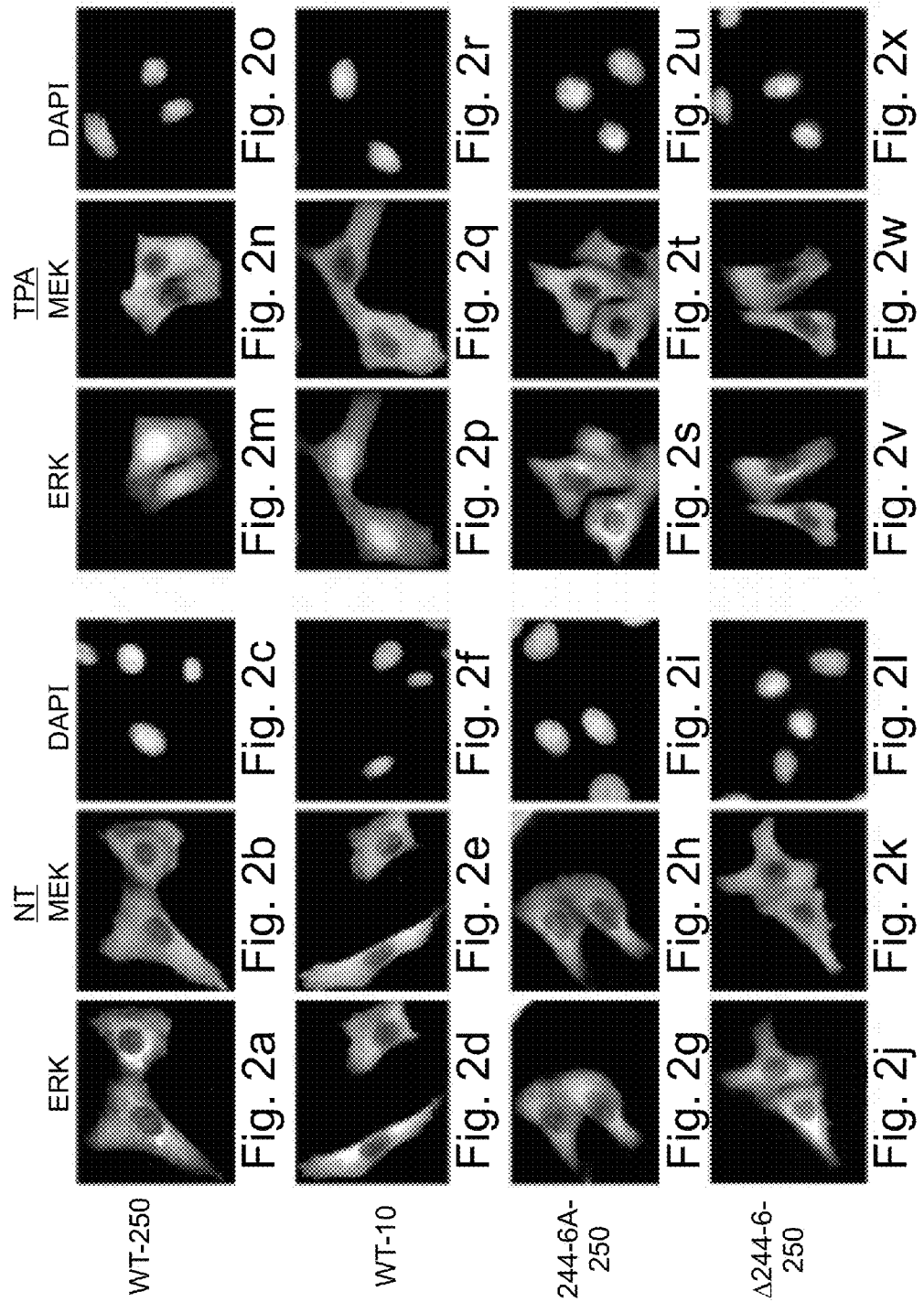

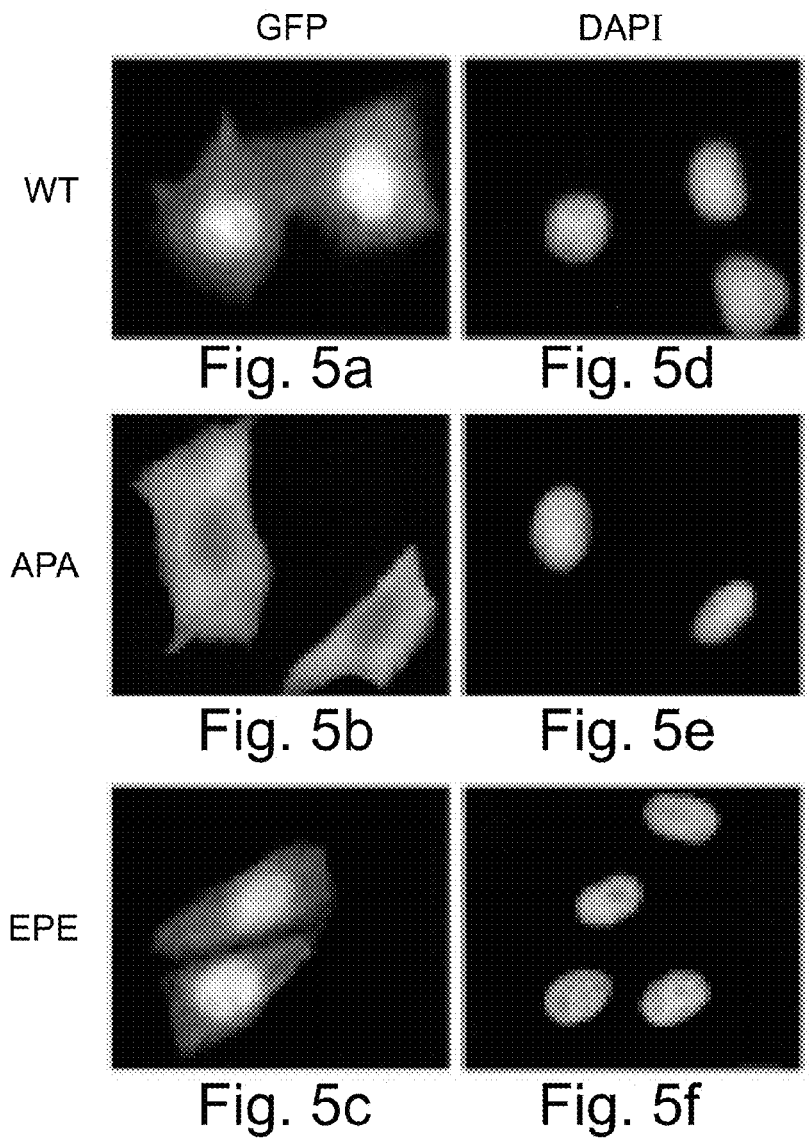
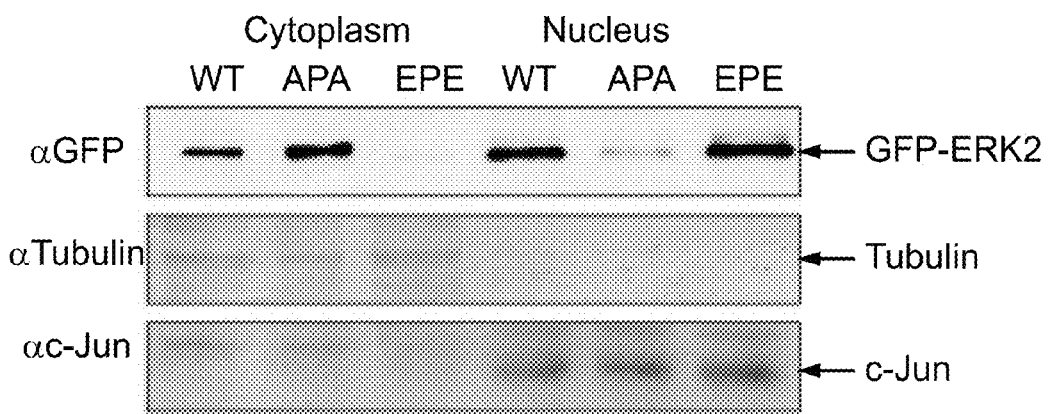
Fig. 6

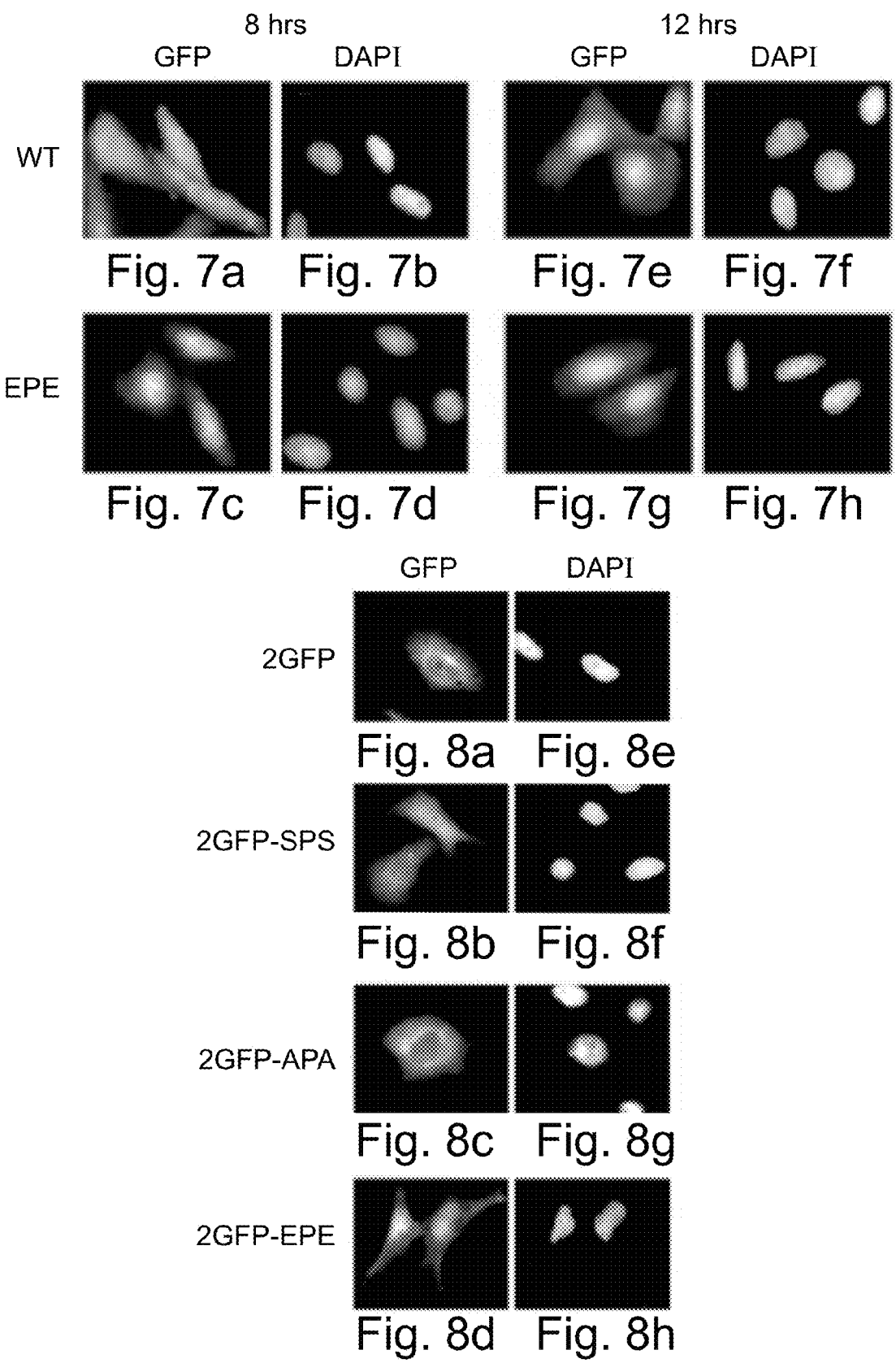

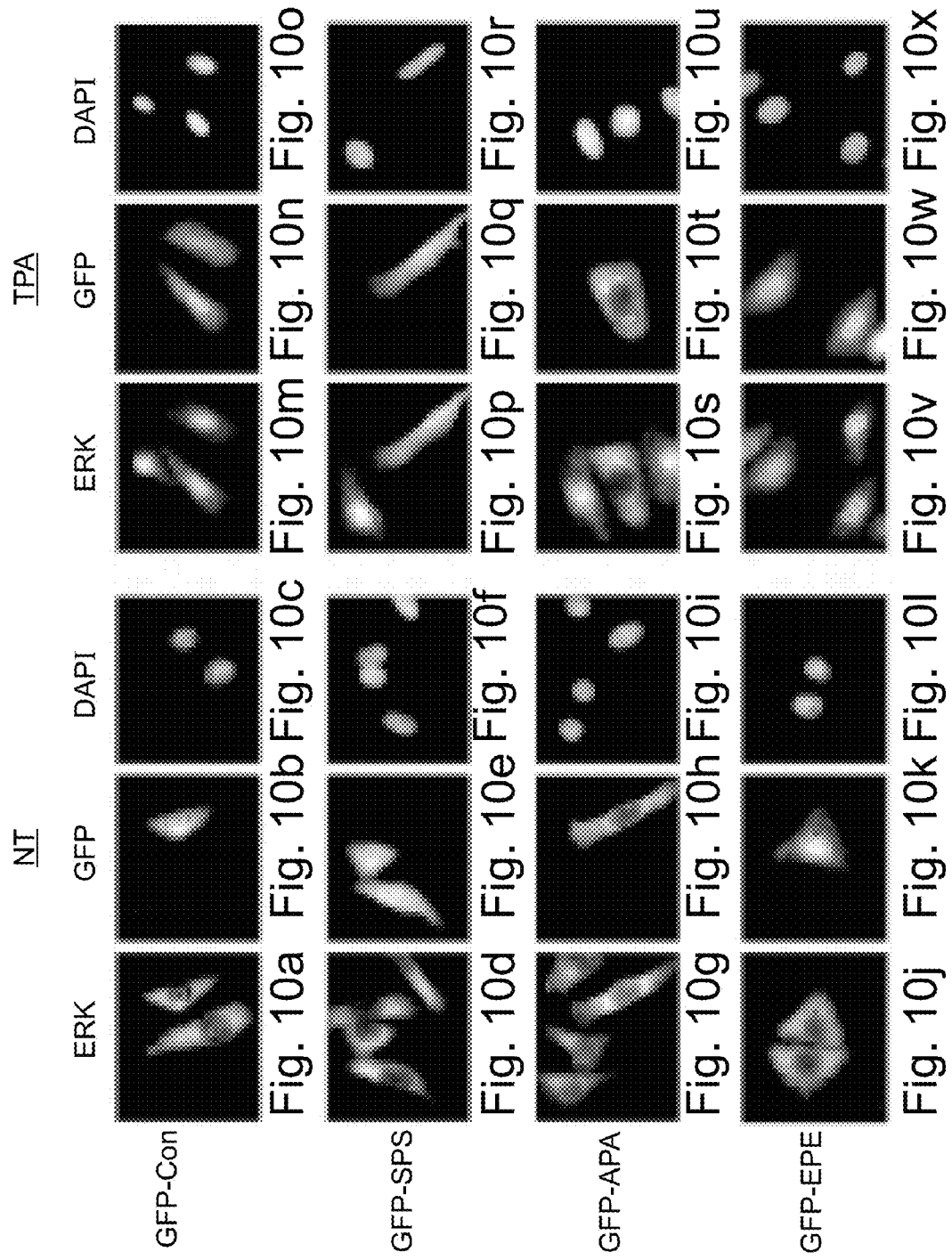

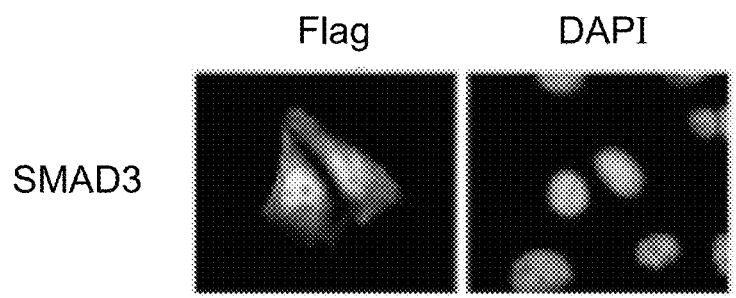
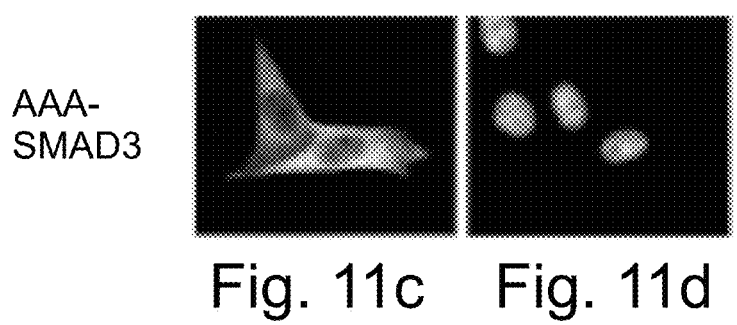
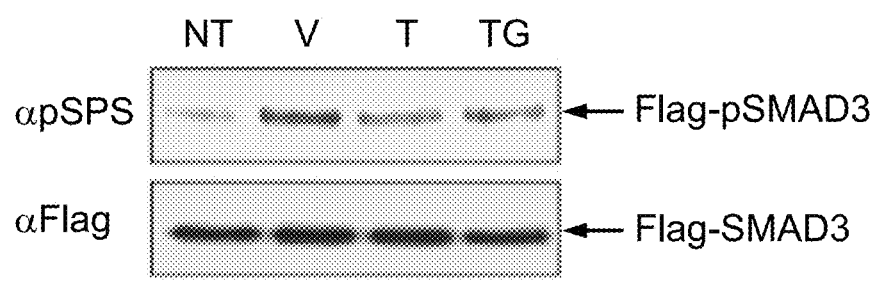
Fig. 11a  Fig. 11b
Fig. 11c  Fig. 11d
Fig. 11e

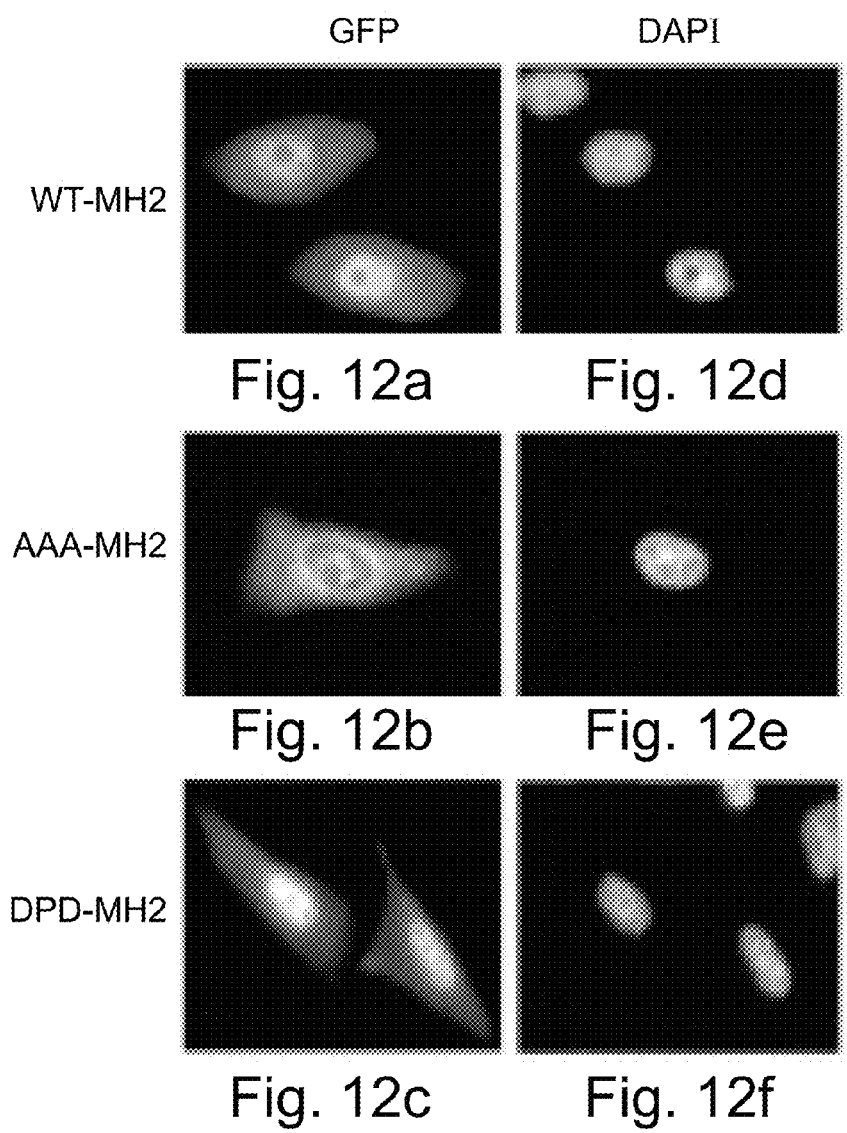
Fig. 12a  Fig. 12d
Fig. 12b  Fig. 12e
Fig. 12c  Fig. 12f
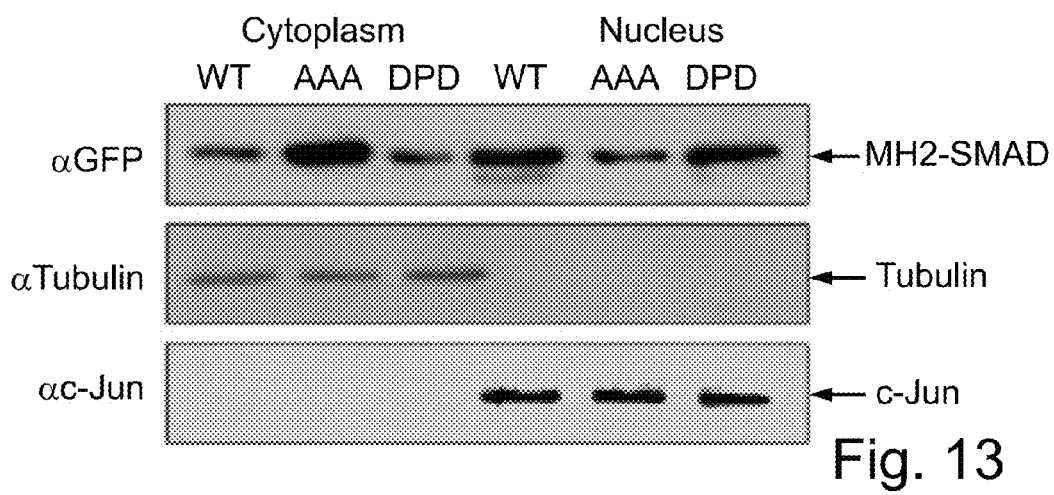
Fig. 13

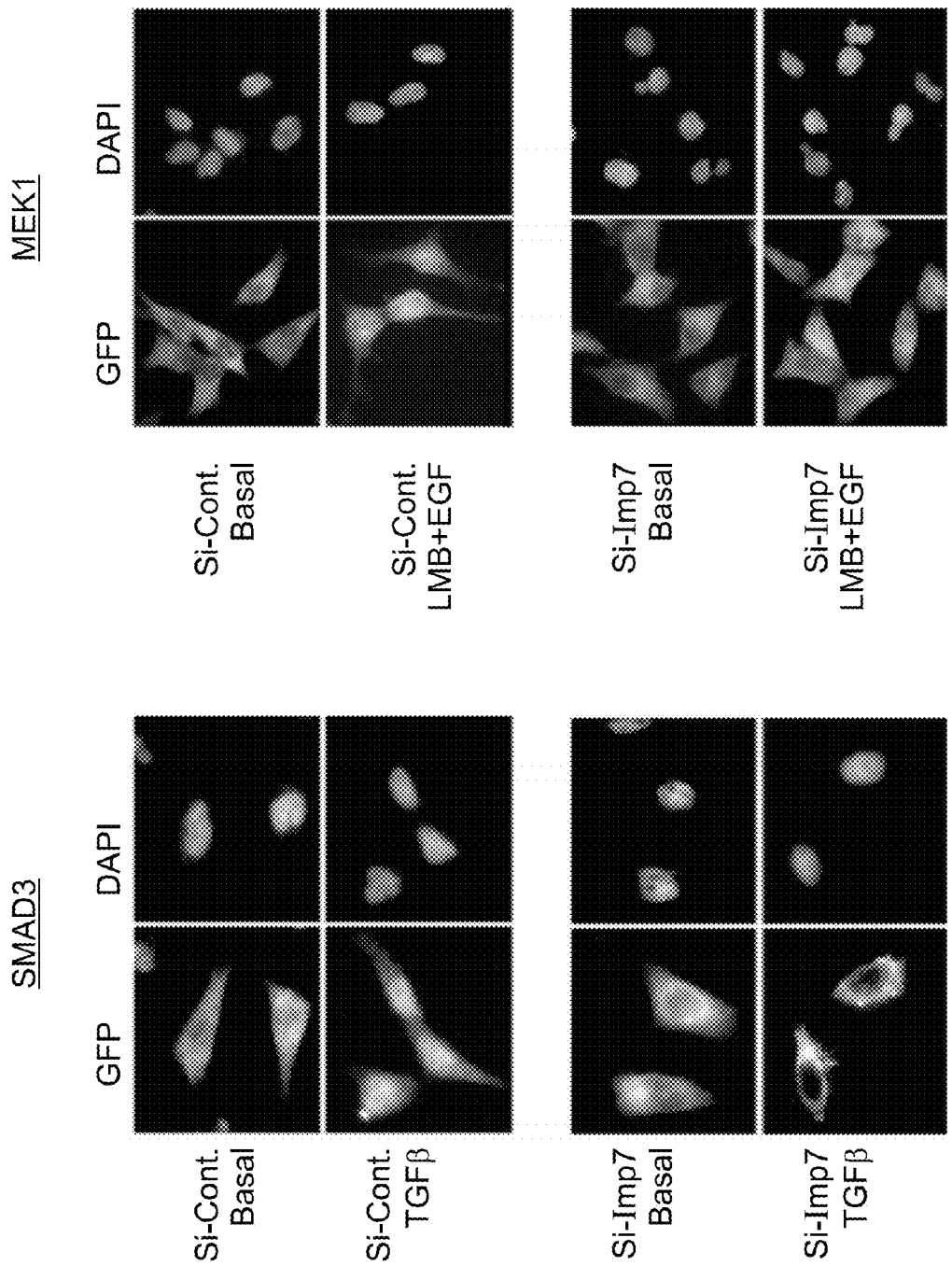

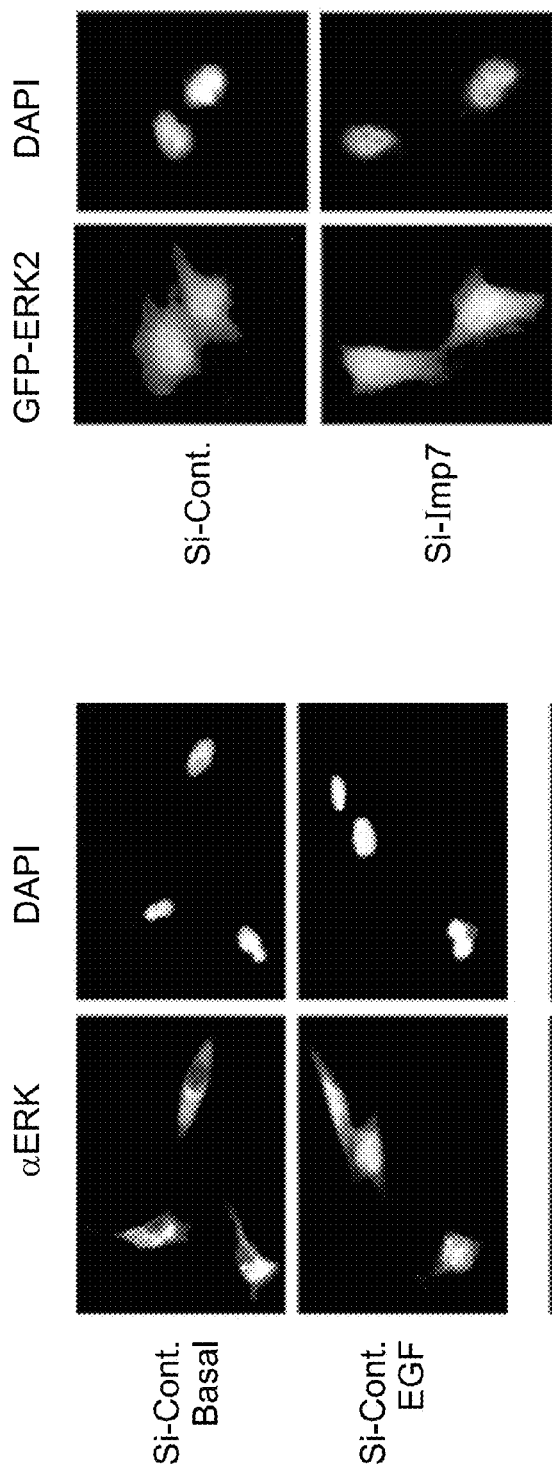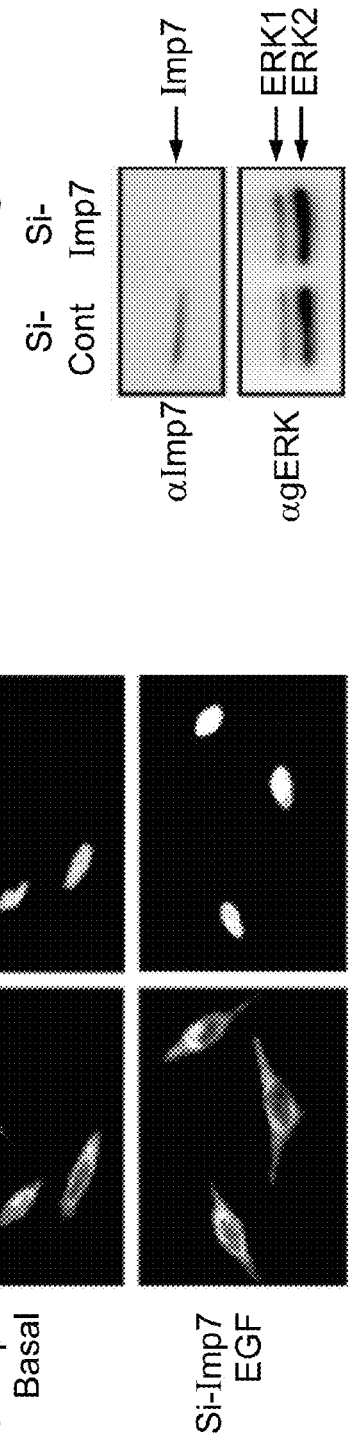

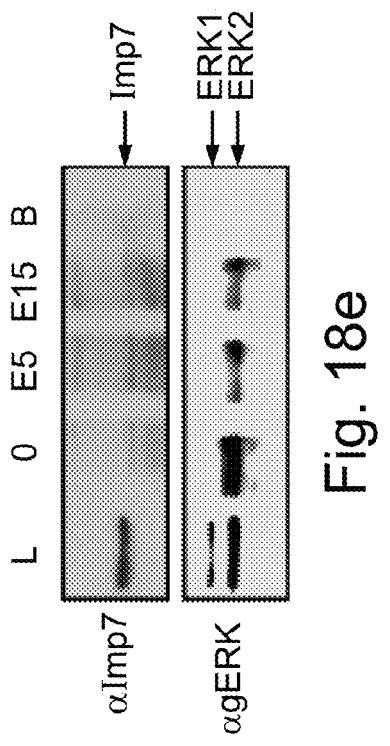
Fig. 18e
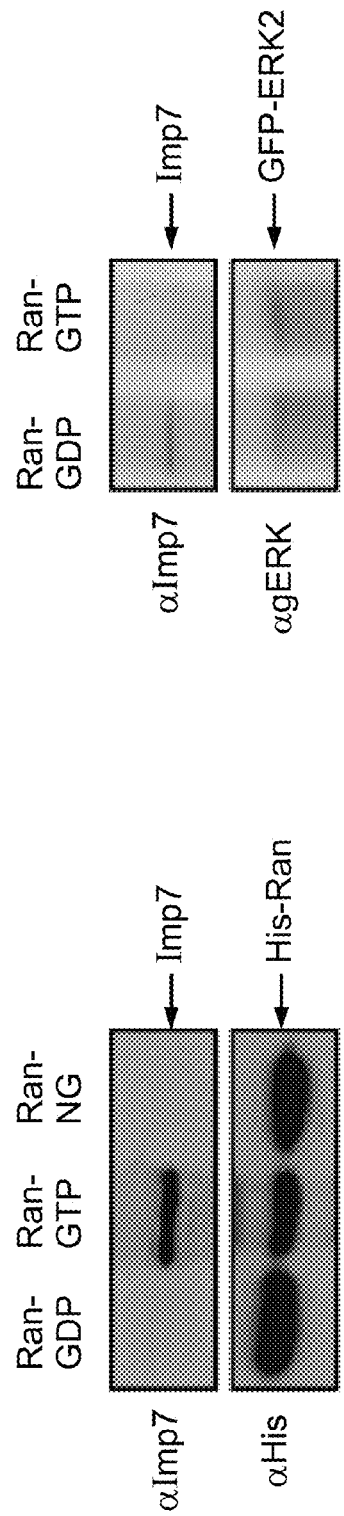
Fig. 18g
Fig. 18d
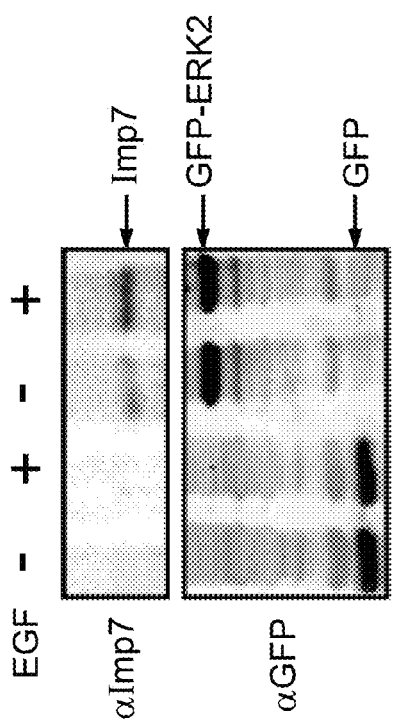
Fig. 18f

```
SMAD3   LQWLDKVLTQMGSPSIRC  404-421
        | |**| |***| |||||
ERK2    LDQLNHILGILGSPSQED   232-249
         |  **  **|  |
MEK1    WLCSTIGLNQPSTPTHAA   374-391
```

Fig. 20

SEQUENCE LISTING

<160> NUMBER OF SEQ ID NOS: 38

<210> SEQ ID NO 1
<211> LENGTH: 3
<212> TYPE: PRT
<213> ORGANISM: Artificial sequence
<220> FEATURE:
<223> OTHER INFORMATION: Consensus sequence of a nuclear localization
      signal
<220> FEATURE:
<221> NAME/KEY: misc_feature
<222> LOCATION: (1)..(1)
<223> OTHER INFORMATION: can be selected from the group consisting of
      serine, threonine, aspartic acid and glutamic acid
<220> FEATURE:
<221> NAME/KEY: misc_feature
<222> LOCATION: (3)..(3)
<223> OTHER INFORMATION: can be selected from the group consisting of
      serine, threonine, aspartic acid and glutamic acid

<400> SEQUENCE: 1

Xaa Pro Xaa
1

<210> SEQ ID NO 2
<211> LENGTH: 18
<212> TYPE: PRT
<213> ORGANISM: Artificial sequence
<220> FEATURE:
<223> OTHER INFORMATION: A peptide containing the wt SPS nuclear
      localization signal from ERK

<400> SEQUENCE: 2

Leu Asp Gln Leu Asn His Ile Leu Gly Ile Leu Gly Ser Pro Ser Gln
1               5                   10                  15

Glu Asp

<210> SEQ ID NO 3
<211> LENGTH: 18
<212> TYPE: PRT
<213> ORGANISM: Artificial sequence
<220> FEATURE:
<223> OTHER INFORMATION: A peptide containing a Ser to Glu mutated SPS
      nuclear localization signal

<400> SEQUENCE: 3

Leu Asp Gln Leu Asn His Ile Leu Gly Ile Leu Gly Glu Pro Glu Gln
1               5                   10                  15

Glu Asp

<210> SEQ ID NO 4
<211> LENGTH: 18
<212> TYPE: PRT
<213> ORGANISM: Artificial sequence
<220> FEATURE:
<223> OTHER INFORMATION: A peptide containing a consensus mutated SPS
      nuclear localization signal
<220> FEATURE:
<221> NAME/KEY: misc_feature
<222> LOCATION: (13)..(13)
<223> OTHER INFORMATION: can be any amino acid preferably
      non-phosphorylatable
<220> FEATURE:
<221> NAME/KEY: misc_feature
<222> LOCATION: (15)..(15)
<223> OTHER INFORMATION: can be any amino acid preferably
      non-phosphorylatable

<400> SEQUENCE: 4

Leu Asp Gln Leu Asn His Ile Leu Gly Ile Leu Gly Xaa Pro Xaa Gln
1               5                   10                  15

Glu Asp

<210> SEQ ID NO 5
<211> LENGTH: 18
<212> TYPE: PRT
<213> ORGANISM: Artificial sequence
<220> FEATURE:
<223> OTHER INFORMATION: A peptide containing a Ser to Ala mutated SPS
      nuclear localization signal

<400> SEQUENCE: 5

Leu Asp Gln Leu Asn His Ile Leu Gly Ile Leu Gly Ala Pro Ala Gln
1               5                   10                  15

Glu Asp

<210> SEQ ID NO 6
<211> LENGTH: 19
<212> TYPE: PRT
<213> ORGANISM: Artificial sequence

```
<220> FEATURE:
<223> OTHER INFORMATION: A 19 amino acid stretch containing the SPS
      signal of ERK2

<400> SEQUENCE: 6

Leu Asp Gln Leu Asn His Ile Leu Gly Ile Leu Gly Ser Pro Ser Gln
1               5                   10                  15

Glu Asp Leu

<210> SEQ ID NO 7
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 7
cacatcctgg gtattcttgg agctgcagca caggaagat                          39

<210> SEQ ID NO 8
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 8
atcttcctgt gctgcagctc caagaatacc caggatgtg                          39

<210> SEQ ID NO 9
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 9
cctgggtatt cttggagctc cagcacagga agat                               34

<210> SEQ ID NO 10
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 10
atcttcctgt gctggagctc caagaatacc cagg                               34

<210> SEQ ID NO 11
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 11
catcctgggt attcttggag agccagaaca ggaagatctg                         40

<210> SEQ ID NO 12
<211> LENGTH: 40
<212> TYPE: DNA
<213> ORGANISM: Artificial sequence
<220> FEATURE:
<223> OTHER INFORMATION: Single strand DNA oligonucleotide
```

<400> SEQUENCE: 12
cagatcttcc tgttctggct ctccaagaat acccaggatg                40

<210> SEQ ID NO 13
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 13
gtcctcaccc agatgggtgc tgcagccatc cgctgttcca g              41

<210> SEQ ID NO 14
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 14
ctggaacagc ggatggctgc agcacccatc tgggtgagga c              41

<210> SEQ ID NO 15
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 15
gtcctcaccc agatgggcga cccagacatc cgctgttg                  38

<210> SEQ ID NO 16
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 16
caacagcgga tgtctgggtc gcccatctgg gtgaggac                  38

<210> SEQ ID NO 17
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 17
cagcccagcg aaccagaaca tgctgctggc gtc                       33

<210> SEQ ID NO 18
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 18
agcatgttct ggttcgctgg gctggttaag gcc                       33

<210> SEQ ID NO 19
<211> LENGTH: 33

```
<212> TYPE: DNA
<213> ORGANISM: Artificial sequence
<220> FEATURE:
<223> OTHER INFORMATION: Single strand DNA oligonucleotide

<400> SEQUENCE: 19
ccttaaccag cccagcgcag cagcccatgc tgc                                    33

<210> SEQ ID NO 20
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 20
gcagcatggg ctgctgcgct gggctggtta agg                                    33

<210> SEQ ID NO 21
<211> LENGTH: 72
<212> TYPE: DNA
<213> ORGANISM: Artificial sequence
<220> FEATURE:
<223> OTHER INFORMATION: Single strand DNA oligonucleotide

<400> SEQUENCE: 21
tcgaggccac catgcttgac cagctgaatc acatcctggg tattcttgga tctccatcac       60
aggaagatct gc                                                           72

<210> SEQ ID NO 22
<211> LENGTH: 67
<212> TYPE: DNA
<213> ORGANISM: Artificial sequence
<220> FEATURE:
<223> OTHER INFORMATION: Single strand DNA oligonucleotide

<400> SEQUENCE: 22
cagatcttcc tgtgatggag atccaagaat acccaggatg tgattcagct ggtcaagcat       60
ggtggcc                                                                 67

<210> SEQ ID NO 23
<211> LENGTH: 72
<212> TYPE: DNA
<213> ORGANISM: Artificial sequence
<220> FEATURE:
<223> OTHER INFORMATION: Single strand DNA oligonucleotide

<400> SEQUENCE: 23
tcgaggccac catgcttgac cagctgaatc acatcctggg tattcttgga gctccagcac       60
aggaagatct gc                                                           72

<210> SEQ ID NO 24
<211> LENGTH: 67
<212> TYPE: DNA
<213> ORGANISM: Artificial sequence
<220> FEATURE:
<223> OTHER INFORMATION: Single strand DNA oligonucleotide

<400> SEQUENCE: 24
cagatcttcc tgagctggtg ctccaagaat acccaggatg tgattcagct ggtcaagcat       60
ggtggcc                                                                 67

<210> SEQ ID NO 25
```

-continued

```
<211> LENGTH: 72
<212> TYPE: DNA
<213> ORGANISM: Artificial sequence
<220> FEATURE:
<223> OTHER INFORMATION: Single strand DNA oligonucleotide

<400> SEQUENCE: 25
tcgaggccac catgcttgac cagctgaatc acatcctggg tattcttgga gagccagagc    60
aggaagatct gc                                                        72

<210> SEQ ID NO 26
<211> LENGTH: 73
<212> TYPE: DNA
<213> ORGANISM: Artificial sequence
<220> FEATURE:
<223> OTHER INFORMATION: Single strand DNA oligonucleotide

<400> SEQUENCE: 26
aattcgcaga tcttcctgct ctggctctcc aagaataccc aggatgtgat tcagctggtc    60
aagcatggtg gcc                                                       73

<210> SEQ ID NO 27
<211> LENGTH: 11
<212> TYPE: PRT
<213> ORGANISM: Artificial sequence
<220> FEATURE:
<223> OTHER INFORMATION: TAT-leader sequence

<400> SEQUENCE: 27

Tyr Ala Arg Ala Ala Ala Arg Gln Ala Arg Ala
1               5                   10

<210> SEQ ID NO 28
<211> LENGTH: 21
<212> TYPE: DNA
<213> ORGANISM: Artificial sequence
<220> FEATURE:
<223> OTHER INFORMATION: SiRNA oligonucleotide

<400> SEQUENCE: 28
gaagaucgcc auuguauucu u                                              21

<210> SEQ ID NO 29
<211> LENGTH: 21
<212> TYPE: DNA
<213> ORGANISM: Artificial sequence
<220> FEATURE:
<223> OTHER INFORMATION: SiRNA oligonucleotide

<400> SEQUENCE: 29
ggaaucugcu uacaggucau u                                              21

<210> SEQ ID NO 30
<211> LENGTH: 21
<212> TYPE: DNA
<213> ORGANISM: Artificial sequence
<220> FEATURE:
<223> OTHER INFORMATION: SiRNA oligonucleotide

<400> SEQUENCE: 30
guauuggccu gaucgagaau u                                              21

<210> SEQ ID NO 31
<211> LENGTH: 21
<212> TYPE: DNA
```

```
<213> ORGANISM: Artificial sequence
<220> FEATURE:
<223> OTHER INFORMATION: SiRNA oligonucleotide

<400> SEQUENCE: 31
gcacugacuc acgucuuau u                                              21

<210> SEQ ID NO 32
<211> LENGTH: 18
<212> TYPE: PRT
<213> ORGANISM: Homo sapiens
<220> FEATURE:
<221> NAME/KEY: misc_feature
<223> OTHER INFORMATION: SMAD3 nuclear localization signal

<400> SEQUENCE: 32

Leu Gln Trp Leu Asp Lys Val Leu Thr Gln Met Gly Ser Pro Ser Ile
1               5                   10                  15

Arg Cys

<210> SEQ ID NO 33
<211> LENGTH: 18
<212> TYPE: PRT
<213> ORGANISM: Homo sapiens
<220> FEATURE:
<221> NAME/KEY: misc_feature
<223> OTHER INFORMATION: ERK2 nuclear localization signal

<400> SEQUENCE: 33

Leu Asp Gln Leu Asn His Ile Leu Gly Ile Leu Gly Ser Pro Ser Gln
1               5                   10                  15

Glu Asp

<210> SEQ ID NO 34
<211> LENGTH: 18
<212> TYPE: PRT
<213> ORGANISM: Homo sapiens
<220> FEATURE:
<221> NAME/KEY: misc_feature
<223> OTHER INFORMATION: MEK1 nuclear localization signal

<400> SEQUENCE: 34

Trp Leu Cys Ser Thr Ile Gly Leu Asn Gln Pro Ser Thr Pro Thr His
1               5                   10                  15

Ala Ala

<210> SEQ ID NO 35
<211> LENGTH: 9
<212> TYPE: PRT
<213> ORGANISM: Human immunodeficiency virus

<400> SEQUENCE: 35

Leu Pro Pro Leu Glu Arg Leu Thr Leu
1               5

<210> SEQ ID NO 36
<211> LENGTH: 9
<212> TYPE: PRT
<213> ORGANISM: Artificial sequence
<220> FEATURE:
<223> OTHER INFORMATION: Concensus sequence for a nuclear export signal
<220> FEATURE:
<221> NAME/KEY: misc_feature
<222> LOCATION: (2)..(3)
<223> OTHER INFORMATION: Xaa can be any naturally occurring amino acid
<220> FEATURE:
```

```
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 36

Leu Xaa Xaa Leu Xaa Xaa Leu Xaa Leu
1               5

<210> SEQ ID NO 37
<211> LENGTH: 7
<212> TYPE: PRT
<213> ORGANISM: Homo sapiens

<400> SEQUENCE: 37

Gly Ser Pro Ser Gln Glu Asp
1               5

<210> SEQ ID NO 38
<211> LENGTH: 18
<212> TYPE: PRT
<213> ORGANISM: Artificial Sequence
<220> FEATURE:
<223> OTHER INFORMATION: oligopeptide
<220> FEATURE:
<221> NAME/KEY: MISC_FEATURE
<222> LOCATION: (13)..(13)
<223> OTHER INFORMATION: Xaa can be Thr, Asp or Glu
<220> FEATURE:
<221> NAME/KEY: MISC_FEATURE
<222> LOCATION: (15)..(15)
<223> OTHER INFORMATION: Xaa can be Thr, Asp or Glu

<400> SEQUENCE: 38

Leu Asp Gln Leu Asn His Ile Leu Gly Ile Leu Gly Xaa Pro Xaa Gln
1               5                   10                  15
Glu Asp
```

NUCLEAR TARGETING SEQUENCES

RELATED APPLICATIONS

This application is a division of U.S. patent application Ser. No. 12/528,465 filed on Aug. 25, 2009, which is a National Phase of PCT Patent Application No. PCT/IL2008/000249 having International filing date of Feb. 28, 2008, which claims the benefit of priority of U.S. Provisional Patent Application No. 60/903,852 filed on Feb. 28, 2007.

The contents of the above applications are all incorporated by reference as if fully set forth herein in their entirety.

SEQUENCE LISTING STATEMENT

The ASCII file, entitled 58742SequenceListing.txt, created on Apr. 3, 2014, comprising 9,941 bytes, submitted concurrently with the filing of this application is incorporated herein by reference.

FIELD AND BACKGROUND OF THE INVENTION

The present invention relates to the translocation of proteins and other compounds into and out of the cell nucleus and, more particularly, to novel nuclear localization signal sequences.

To ensure accurate cellular functioning, the spatial distribution of proteins needs to be tightly regulated and coordinated. This is particularly apparent in many signaling proteins that dynamically and rapidly change their localization upon extracellular stimulation. In order to maintain such regulation, the nucleus is separated from the cytoplasm by a double membrane envelope that allows for a selective entrance of proteins through specialized nuclear pore complexes (NPC). The selectivity of nuclear localization is primarily mediated by a nuclear localization signal (NLS) harbored within the sequence of the nuclear protein [G. Schlenstedt, FEBS Lett 389, 75 (Jun. 24, 1996)].

The major type of NLS identified thus far is composed of basic amino acids which are required for the mechanism of entrance through the NPC. These basic sequences come in two flavors: (i) a single stretch of five to six basic amino acids, exemplified by the simian virus (SV) 40 large T antigen NLS; and (ii) a bipartite NLS composed of two basic amino acids, a spacer region of 10-12 amino acids, and a cluster in which three of five amino acids must be basic. This type is typified by nucleoplasmin. For NLS-mediated nuclear import to occur, the NLS first associates with the cytosolic import-receptor proteins importin α and β, which allows docking at the cytoplasmic side of the nuclear pore [E. J. Tran, S. R. Wente, Cell 125, 1041 (Jun. 16, 2006)]. Movement through the nuclear pore is regulated by the small GTPase Ran, which in its GTP-bound state promotes the dissociation of the imported protein from the importins and their recycling back to the cytoplasm [J. Moroianu, J Cell Biochem Suppl 32-33, 76 (1999)].

However, not all cyto-nuclear shuttling proteins contain the canonical NLS, and therefore use other, NLS-independent, mechanisms for their passage through the NPC. Some of the characterized NLS-independent mechanisms include passive diffusion of small proteins (<30-40 kDa), distinct nuclear-directing motifs [D. Christophe, C. Christophe-Hobertus, B. Pichon, *Cell Signal* 12, 337 (May, 2000)], interaction with NLS-containing proteins, or alternatively a direct interaction with the nuclear pore proteins (NUPs); [L. Xu, J. Massague, Nat Rev Mol Cell Biol 5, 209 (March, 2004)]. However, the kinetics of shuttling and nuclear retention by these mechanisms are usually too slow to allow timely transient transcription, and therefore the molecular mechanism(s) that allows the rapid and reversible NLS-independent translocation of signaling proteins upon stimulation is still obscure.

Examples of signaling proteins that translocate into the nucleus upon stimulation, in an NLS-independent manner include ERKs, MEKs and SMADs. The importance of these proteins in the regulation of proliferation and differentiation led to many studies on the nuclear translocation of both ERKs and SMAD3. Although a possible involvement of the canonical NLS machinery was initially suggested in some systems, it is now thought that these proteins may translocate into the nucleus via their direct interaction with NUPs [L. Xu, J. Massague, Nat Rev Mol Cell Biol 5, 209 (March, 2004)].

Once in the nucleus, many proteins are transported back to the cytoplasm as an essential step in their biological function. The export of macromolecules from the nucleus also relies on the existence of a specific signal in the substrate to be exported. For example, the Rev protein of human immunodeficiency virus type 1 (HIV-1) exits the nucleus, facilitating export of the unspliced viral RNA [Pollard and Malim, Ann. Rev. Microbiol., 52:491-532, 1998]. Rev protein nuclear export is mediated by a specific nuclear export signal (NES) sequence consisting of the leucine-rich sequence, LPPLER-LTL (SEQ ID NO: 35), found also in proteins of other viruses [Dobbelstein et al., EMBO J. 16:4276-4284, 1997]. Additionally, numerous cellular proteins, such as I-KB and MEK, contain NES that regulate the biological activity of these proteins by controlling their nuclear export [Ullman et al., Cell 90:967-970, 1997]. The consensus sequence of NES is LXXLXXLXL (SEQ ID NO: 36) and it was shown that this type of sequence interacts with proteins named exportins that mediate a rapid export of the shuttling proteins.

The ability to regulate the cellular localization of a biological component is important for many functions such as the regulation of nucleic acid expression, transfection of eukaryotic cells, gene therapy, protection from toxic chemicals and transport of anti-cancer agents. There is thus a widely recognized need for, and it would be highly advantageous to identify novel sequences capable of regulating nuclear translocation.

SUMMARY OF THE INVENTION

According to one aspect of the present invention there is provided an isolated peptide comprising an amino acid sequence being no more than 20 amino acids in length, the amino acid sequence comprising:

$X_1 X_2 X_3$;

wherein $X_1$ and $X_3$ are each independently selected from the group consisting of serine, threonine, aspartic acid and glutamic acid;

wherein $X_2$ is proline, the isolated peptide comprising a nuclear targeting activity.

According to another aspect of the present invention there is provided an isolated peptide comprising an amino acid sequence at least 70% homologous to a sequence as set forth by:

(SEQ ID NO: 4)
L D Q L N H I L G I L G $X_1$ P $X_2$ Q E D;

wherein $X_1$ and $X_2$ are any amino acid, the isolated peptide being capable of preventing ERK nuclear translocation.

According to yet another aspect of the present invention there is provided a composition of matter comprising the isolated peptide comprising an amino acid sequence being no more than 20 amino acids in length, the amino acid sequence comprising:

$X_1 X_2 X_3$;

wherein $X_1$ and $X_3$ are each independently selected from the group consisting of serine, threonine, aspartic acid and glutamic acid;

wherein $X_2$ is proline, the isolated peptide comprising a nuclear targeting activity, and a heterologous substance linked to the amino acid sequence via a linker.

According to still another aspect of the present invention there is provided an isolated polynucleotide comprising a nucleic acid sequence encoding a peptide comprising an amino acid sequence being no more than 20 amino acids in length, the amino acid sequence comprising:

$X_1 X_2 X_3$;

wherein $X_1$ and $X_3$ are each independently selected from the group consisting of serine, threonine, aspartic acid and glutamic acid;

wherein $X_2$ is proline, the isolated peptide comprising a nuclear targeting activity.

According to still another aspect of the present invention there is provided an isolated polynucleotide comprising a nucleic acid sequence encoding a peptide comprising an amino acid sequence at least 70% homologous to a sequence as set forth by:

```
                                           (SEQ ID NO: 4)
     L D Q L N H I L G I L G X₁ P X₂ Q E D;
``` wherein $X_1$ and $X_2$ are any amino acid, the isolated peptide being capable of preventing ERK nuclear translocation.

According to an additional aspect of the present invention there is provided a nucleic acid construct comprising the isolated polynucleotides of the present invention.

According to yet an additional aspect of the present invention there is provided an isolated cell comprising the nucleic acid construct of the present invention.

According to still an additional aspect of the present invention there is provided a method of targeting a substance into a nucleus of a host cell, the method comprising introducing the substance into the host cell, the substance being attached to the peptide of the present invention.

According to a further aspect of the present invention there is provided a method of targeting a substance into a nucleus of a host cell, the method comprising introducing the peptide of the present invention into the host cell, the peptide being linked to an affinity moiety capable of recognizing the substance.

According to yet a further aspect of the present invention there is provided a pharmaceutical composition comprising as an active agent the nucleic acid construct of the present invention and a pharmaceutically acceptable carrier.

According to still a further aspect of the present invention there is provided a pharmaceutical composition comprising as an active agent the composition of matter of the present invention and a pharmaceutically acceptable carrier.

According to still a further aspect of the present invention there is provided a pharmaceutical composition comprising as an active agent the peptide of the present invention and a pharmaceutically acceptable carrier.

According to still a further aspect of the present invention there is provided a method of identifying an agent capable of modulating serine and/or threonine phosphorylation, the method comprising:

(a) introducing a molecule into a host cell, wherein the molecule comprises:

i. an isolated peptide comprising an amino acid sequence being no more than 20 amino acids in length, the amino acid sequence comprising:

$X_1 X_2 X_3$;

wherein $X_1$ and $X_3$ are each independently serine or threonine;

wherein $X_2$ is proline; and ii. a detectable moiety; and (b) analyzing a location of the molecule in a presence and an absence of the agent, wherein a change in location of said molecule is indicative of an agent capable of modulating serine and/or threonine phosphorylation.

According to still a further aspect of the present invention there is provided a method of treating a hyperproliferative disease in a subject, the method comprising administering to the subject a therapeutically effective amount of the isolated peptide of the present invention into the subject, thereby treating the hyperproliferative disease.

According to further features in preferred embodiments of the invention described below, at least one of the amino acids is a naturally occurring amino acid.

According to still further features in the described preferred embodiments at least one of the amino acids is a synthetic amino acid.

According to still further features in the described preferred embodiments at least one of the amino acids is a D stereoisomer.

According to still further features in the described preferred embodiments at least one of the amino acids is an L stereoisomer.

According to still further features in the described preferred embodiments, the nuclear targeting activity is regulatable.

According to still further features in the described preferred embodiments, the nuclear targeting activity is constitutive.

According to still further features in the described preferred embodiments, the heterologous substance is linked to the amino acid sequence via a linker.

According to still further features in the described preferred embodiments, the peptide is as set forth in SEQ ID NO: 2.

According to still further features in the described preferred embodiments, the peptide is as set forth in SEQ ID NO: 3.

According to still further features in the described preferred embodiments, the $X_1$ and $X_2$ do not comprise an amino acid selected from the group consisting of serine, threonine, aspartic acid and glutamic acid.

According to still further features in the described preferred embodiments, the peptide is as set forth by SEQ ID NO: 5.

According to still further features in the described preferred embodiments, the heterologous substance is selected from the group consisting of a polypeptide a nucleic acid, a small molecule and a carbohydrate.

According to still further features in the described preferred embodiments, the heterologous substance is a polypeptide.

According to still further features in the described preferred embodiments, the heterologous substance is a pharmaceutical agent.

According to still further features in the described preferred embodiments, the pharmaceutical agent is a therapeutic agent, a cosmetic agent or a diagnostic agent.

According to still further features in the described preferred embodiments, the composition of matter is linked to a detectable moiety via a linker.

According to still further features in the described preferred embodiments, the linker comprises a peptide bond.

According to still further features in the described preferred embodiments, the linker comprises a non-peptide bond.

According to still further features in the described preferred embodiments, the composition of matter is linked to an affinity moiety via a linker.

According to still further features in the described preferred embodiments, the affinity moiety is selected from the group consisting of an antibody, a receptor ligand and a carbohydrate.

According to still further features in the described preferred embodiments, the nuclear targeting activity is regulatable.

According to still further features in the described preferred embodiments, the nuclear targeting activity is constitutive.

According to still further features in the described preferred embodiments, the nucleic acid construct further comprises a cis regulatory element for regulating expression of the polynucleotide.

According to still further features in the described preferred embodiments, the isolated polynucleotide is transcriptionally fused to a nucleic acid sequence encoding a heterologous polypeptide sequence of interest.

According to still further features in the described preferred embodiments, the isolated cell is eukaryotic.

According to still further features in the described preferred embodiments, the eukaryotic cell is a yeast cell.

According to still further features in the described preferred embodiments, the substance is an endogenous substance.

According to still further features in the described preferred embodiments, the substance is an exogenous substance.

According to still further features in the described preferred embodiments, the method further comprises administering said exogenous substance into the host cell prior to, concomitant with or following the introducing.

According to still further features in the described preferred embodiments, the host cell is a dividing cell.

According to still further features in the described preferred embodiments, the host cell is a non-dividing cell.

According to still further features in the described preferred embodiments, the substance is selected from the group consisting of a polypeptide, a nucleic acid, a small molecule and a carbohydrate.

According to still further features in the described preferred embodiments, the substance is a nucleic acid.

According to still further features in the described preferred embodiments, the nucleic acid is introduced into the host cell by a method selected from the group consisting of: microinjection, electroporation, calcium phosphate coprecipitation, DEAE dextran introduction, liposome mediated introduction, viral mediated introduction, naked DNA injection, and biolistic bombardment.

According to still further features in the described preferred embodiments, the targeting is effected in vivo.

According to still further features in the described preferred embodiments, the targeting is effected ex vivo.

According to still further features in the described preferred embodiments, the targeting is effected in vitro.

According to still further features in the described preferred embodiments, the host cell is a eukaryotic cell.

According to still further features in the described preferred embodiments, the eukaryotic cell is a yeast cell.

According to still further features in the described preferred embodiments, the method further comprises activating phosphorylation of the polypeptide of the present invention in the host cell following the introducing.

According to still further features in the described preferred embodiments, the activating phosphorylation is effected by an agent selected from the group consisting of TPA, VOOH, TGFβ and EGF.

According to still further features in the described preferred embodiments, the detectable moiety is non-directly detectable.

According to still further features in the described preferred embodiments, the non-directly detectable moiety is a substrate for an enzymatic reaction capable of generating a detectable product.

According to still further features in the described preferred embodiments, the detectable moiety is directly detectable.

According to still further features in the described preferred embodiments, the directly detectable moiety is selected from the group consisting of a phosphorescent agent, a chemiluminescent agent and a fluorescent agent.

According to still further features in the described preferred embodiments, the hyperproliferative disease is cancer.

The present invention successfully addresses the shortcomings of the presently known configurations by providing novel nuclear translocation signals.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-R are photomicrographs illustrating the role of SPS in the non-regulated accumulation of ERK2 in the nucleus. CHO (FIGS. 1A-F and 1M-R) or COS7 cells (FIGS. 1G-L) were grown on cover slips and transfected with WT-ERK2, or the mutants 244-6A and Δ244-6. Twenty-four hr following transfection, the cells were serum-starved (16 hr), fixed, stained with DAPI and visualized using a fluorescent microscope.

FIGS. 2A-X are photomicrographs illustrating the role of SPS in the stimulated nuclear translocation of ERK2. CHO cells were grown on cover slips and cotransfected with HA-MEK1 together with either WT-ERK2, 244-6A, or Δ244-6. Twenty-four hr after transfection, the cells were serum starved for 16 hours, treated with TPA (250 nM, 15 min), except in WT-10 where the cells were treated with 10 nM TPA for 15 min. After treatments the cells were fixed and stained with either anti-HA Ab or DAPI.

FIG. 4A illustrates an elevation of pSPS detection upon stimulation. COS cells were transfected with WT-GFP-ERK2. Twenty-four hr after transfection, the cells were serum-starved for 16 hr and subsequently treated with the general stimulator VOOH (V, 100 μM $Na_3VO_4$ and 200 μM $H_2O_2$, 15 min), TPA (T, 250 nM, 15 min), EGF (E, 50 ng/ml for 15 min), or left untreated (NT). The GFP-ERK2 was immunoprecipitated with anti GFP Ab, extensively washed, and the IP was then subjected to Western blotting with anti phospho SPS-ERK (αphoSPS-ERK) and anti general ERK (αgen-ERK) Abs. FIG. 4B is a time course of SPS phosphorylation. COS7 cells overexpressing WT-GFP-ERK2 were serum starved followed by EGF stimulation for the indicated time points. The lysates were then subjected to Western blot analysis as in FIG. 4A. FIGS. 4C-D. GFP-ERK2 was immunoprecipitated from VOOH stimulated (Act) or non-stimulated (NT), transfected COS7 cells as above. The immunoprecipitated protein was then incubated with shrimp's alkaline phosphates (SAP, 15 units, 30 min, 30° C. in the manufacturer digestion buffer), and subjected to Western blot analysis with anti phosphoSPS-ERK (αpSPS; FIG. 4C), anti phosphoTEY-ERK (αpTEY; FIG. 4D), and anti general-ERK Ab (αgen-ERK; FIGS. 4C, D). FIG. 4E. Elevation of anti pSPS Ab immunoreactivity upon stimulation of endogenous ERKs. Following serum starvation COS7 cells were treated with EGF (50 ng/ml) or VOOH (V, 100 μM $Na_3VO_4$ and 200 μM $H_2O_2$) for the indicated times. SPS phosphorylation was detected using the anti pSPS Abs, and this was compared to the amount of general ERKs detected by αgERK. FIG. 4F. Specificity of the anti pSPS Ab. COS7 cells overexpressing either GFP-ERK2 or 244-6A mutant were serum starved for 16 hr, and then treated with EGF (50 ng/ml) for 15 min following WB analysis using αpSPS and αgERK Abs. FIG. 4G. TEY phosphorylation is not required for SPS phosphorylation. COS7 cells overexpressing WT-ERK2 or TEY-AAA were treated as described in D. FIG. 4H. COS7 cells were treated with or without UO126 prior (15 min) to EGF (50 ng/ml) stimulation for the indicated times. SPS-phosphorylation was detected using αpSPS and αgERK Abs. FIG. 4I. Phosphorylation of SPS is mediated by ERK autophosphorylation. Immunoprecipitated, stringently washed WT-ERK2, TEY-AAA or ERK-APA (SPS-APA) were subjected to in vitro kinase assay where GST-ERK2 (GST-ERK), Act-GST-ERK2 (Act-ERK) or GST-KA-ERK2 (KA-ERK) act as a kinase. The phosphorylation ($^{32}$P-ERK2) of ERK and its mutants was detected by autoradiography. Equal loading was confirmed by WB using anti gERK Ab.

FIGS. 5A-F are photomicrographs illustrating that mutating the Ser residues in the SPS to Glu induces the nuclear accumulation of ERK2. CHO cells were grown on cover slips and transfected with WT-GFP-ERK2 (WT), APA-GFP-ERK2 (APA), or EPE-GFP-ERK2 (EPE). Twenty-four hr after transfection, the cells were serum-starved, fixed, stained with DAPI and visualized by a fluorescent microscope.

FIG. 6 is an autoradiograph illustrating the subcellular fractionation of WT-GFP-ERK2 (WT), APA-GFP-ERK2 (APA), or EPE-GFP-ERK2 (EPE). COS7 cells were grown in 10 cm plates and transfected with the above ERK2 constructs. Twenty-four hr after transfection the cells were serum-starved for 16 hr and subjected to cellular fractionation as described under materials and Methods. Western blot analysis of aliquots of the fractions were stained with anti GFP Ab to detect the ERK2 and its mutant, and with anti tubulin and anti c-Jun Abs as markers for the cytoplasmic and nuclear fractions respectively.

FIGS. 7A-H are photomicrographs illustrating that EPE-ERKs translocates to the nucleus faster than WT-ERK. CHO cells were transfected with WT-GFP-ERK2 (WT) and EPE-GFP-ERK2 (EPE). Eight (FIGS. 7A-D) or twelve (FIGS. 7E-H) hours after transfection the cells were fixed, stained with DAPI and visualized by a fluorescent microscope.

FIGS. 8A-H are photomicrographs illustrating that SPS, APA, and EPE peptides fused to a 2GFP chimera modify its subcellular localization. CHO cells were grown on cover slips and transfected with 19 amino acid from the kinase insert domain of ERK2 including the SPS region (GFP-SPS) fused to a 2GFP chimera and with the same chimeras with substitution of the Ser to Ala (GFP-APA) or substitution to Glu (GFP-EPE). Twenty-four hr later, the cells were serum-starved for 16 hr, fixed, stained with DAPI and visualized by a fluorescence microscope.

FIGS. 10A-X illustrate the effects of the 2GFP chimeras on the nuclear translocation of endogenous ERKs. CHO cells overexpressing 2GFP, 2GFP-SPS, 2GFP-APA and 2GFP-EPE were serum starved and treated with or without TPA (250 nM, 15 min). Subsequently, the cells were fixed and stain with anti-ERK2 (C-14) Ab and with DAPI.

FIGS. 11A-D are photomicrographs illustrating that mutation of SPS prevents the nuclear translocation of full length SMAD3. CHO cells overexpressing either Flag-SMAD3 (SMAD3) or its AAA mutant (AAA-SMAD3) were fixed and stained both with anti Flag Ab and DAPI.

FIG. 11E is an autoradiograph illustrating elevation of pSPS detection upon stimulation on SMAD3. COS7 cells overexpressing Flag-SMAD3 were serum starved and then stimulated with (V, 100 μM Na$_3$VO$_4$ and 200 μM H$_2$O$_2$, 15 min), TPA (T, 250 nM, 15 min), TGFβ (TG, 1 ng/ml, 15 min), or left untreated (NT). The FLAG-SMAD3 was immunoprecipitated with anti Flag Ab, extensively washed, and the immunoprecipitated proteins were then subjected to WB with anti-pSPS (αpSPS) or anti-Flag (αFlag) Abs.

FIGS. 12A-F are photomicrographs illustrating that mutants of the SPS domain modulate the subcellular translocation of the MH2 region of SMAD3. CHO cells overexpressing MH2 domain of SMAD3 (WT-MH2), or the AAA (AAA-MH2) and DPD mutant (MH2-DPD) were fixed and visualized under florescent microscope.

FIG. 13 is an autoradiograph illustrating the subcellular fractionation of the MH2 constructs described in COS7 cells. Western blot analysis of aliquots of the fractions were stained with anti GFP Ab to detect the MH2-SMAD3 and its mutant, and with anti tubulin and anti c-Jun Abs as markers for the cytoplasmic and nuclear fractions respectively.

FIGS. 17A-B are photomicrographs illustrating the effect of importin7 depletion on SMAD3 and MEK1 localization. FIG. 17A. TGFβ-induced SMAD3 translocation is prevented by siRNA of importin-7 (SEQ ID NOS: 28-31). Hela cells were transfected with siRNA of importin-7 or control siRNA (scrambled sequence using oligofectamin. Seventy two hours after transfection the cells were serum starved, and then either treated with TGFβ (1 ng/ml; 20 minutes) or left untreated as a control. Subsequently, the cells were washed, fixed and stained with anit-SAMD3 Ab (Cell Signaling USA) and DAPI. FIG. 17B. EGF-induced MEK1 nuclear translocation is partially prevented by siRNA of importin-7. Hela cells were transfected with siRNA against Importin 7 or control siRNA. Seventy two hours after transfection the cells were serum starved, and then either treated with LMB+EGF (5 ng/ml LMB for 45 minutes followed by 50 ng/ml EGF for an additional 15 minutes) or left untreated as a control. Subsequently, the cells were washed, fixed and stained with anti-MEK Ab (Santa Cruz, USA) and DAPI.

FIGS. 18A-G are photomicrographs and autoradiographs illustrating that the active nuclear translocation of ERKs is mediated by importin-7 and Ran-GTP. FIG. 18A. EGF-induced ERKs translocation is prevented by SiRNA of importin-7 (SEQ ID NOS: 28-31). HeLa cells were transfected with SiRNA of importin-7 or scramble control SiRNA using oligofectamin. Seventy two hr after transfection the cells were serum starved as described in FIGS. 1-3, and then either treated with EGF (50 ng/ml, 15 min) or left untreated as a control. Subsequently, the cells were washed, fixed and stain with anti gERK Ab and DAPI. FIG. 18B. Nuclear accumulation of WT-GFP-ERK2 is not affected by SiRNA of importin-7. HeLa cells overexpressing the SiRNA against Importin7 or the control SiRNA (72 hr after transfection) were further cotransfected with WT-GFP-ERK2 (GFP-ERK2). Forty eight hr after this transfection the cells were serum starved, and then fixed and stained with DAPI. FIG. 18C. The SiRNA of importin-7 indeed abolishes its own expression. HeLa cells overexpressing the SiRNA of importin-7 or control SiRNA (72 hr after oligofectamin transfection) were harvested and subjected to WB analysis using anti-importin-7 (αImp7) and anti general ERK (αgERK) Abs. FIG. 18D. GFP-ERK interaction with importin-7 is stimulation-dependent. HeLa cells overexpressing GFP-ERK2 or a control GFP were serum starved and then treated with or without EGF (50 ng/ml, 15 min). This was followed by coimmunoprecipitation using A/G beads pre-conjugated to anti GFP Ab and mild washes. The amount coimmunoprecipitated importin-7 (upper panel) and the amount of immunoprecipitated GFP or GFP-ERK2 (lower panel) were determined by WB analysis using αImp7 and anti-GFP (αGFP) Abs. FIG. 18E. Importin-7 interaction with endogenous ERK2 is elevated by EGF stimulation. Serum-starved HeLa cells were treated with EGF (50 ng/ml) for 0, 5 and 15 min (0, E5 and E15) and then subjected to coimmunoprecipitation using A/G beads pre-conjugated to anti ERK2 Ab or to mock precipitation with beads alone (B). The amount of coimmunoprecipitated importin-7 (upper panel), the amount of the immunoprecipitated ERKs (lower panel) and a loading marker (L) were determined by WB analysis using αImp7 and αgERK Abs. FIG. 18F. Importin-7 interacts with RanGTP but not RanGDP or unloaded Ran. Immunpreciptated importin-7 from HeLa cells was extensively washed, and incubated with 1 μg of 6His-Ran preloaded (1 hr, 4° C.) with GDP (Ran-GDP), GTP (Ran-GTP) or buffer control (No Guanidine, NG). Subsequently, the beads were mildly washed, and subjected to WB analysis using αImp7 and anti His (αHis) Abs. FIG. 18G. Ran-GTP abrogates ERK2-importin-7 interaction. Coimmunoprecipitation of GFP-ERK2 with importin-7 was performed as described in FIG. 18E, in the presence of either 1 μg Ran-GDP or 1 μg Ran-GTP. The amount of coimmunoprecipitated Imp7 and precipitated GFP-ERK2 were detected using αImp7 and αgERK Abs.

FIG. 9A. Interaction of ERK2 with Importin-7 is enhanced by EGF stimulation and EPE mutation. HeLa cells overexpressing WT-ERK (WT), ERK-APA (APA), ERK-EPE (EPE) or GFP were serum starved and treated with EGF (50 ng/ml, 10 min). The extracts of the treated cells were then subjected to coimmunoprecipitation using A/G beads pre-conjugated with anti GFP Ab and mild washes. The coimmunoprecipitated importin-7 (first panel) and importin-13 (third panel), as well as their loading amounts (panels 2 and 4 respectively) were determined by WB using anti importin-7 (αImp7) and importin-β (αImpβ) Abs. The equal amount of immunoprecipitated ERKs was determined with anti GFP (αGFP; IP) Ab. FIG. 19B. Interaction of 2GFP-SPS and its mutants with importin- 7. HeLa cells overexpressing 2GFP, 2GFP-SPS, 2GFP-APA and 2GFP-EPE constructs were subjected to coimmunoprecipitation as described in FIG. 19A (without EGF stimulation). FIG. 19C. Interaction of NUP153 with WTERK2 and its APA and EPE mutants. NUP153c is elevated in APA-ERK2, but reduced in EPE-ERK2. Immunoprecipitated and stringently washed WT-ERK2 (WT), APA-ERK2 (APA) or ERK2 from COST cells pre-treated with or without TPA (250 nM, 15 min) were incubated with 0.5 µg recombinant His-Nup153c. This was followed by mild washing, and the beads were then subjected to Western blot analysis using anti His (αHis) and anti αGFP Abs.

FIG. 20 is a sequence alignment between the NTS region of ERK2, SMAD3 and MEK1 (SEQ ID NOs: 32, 33 and 34 respectively). All sequences are of human origin.

DESCRIPTION OF THE PREFERRED EMBODIMENTS

The present invention is of novel nuclear translocation signals which can be used to direct a heterologous substance (either constitutively, or in a regulatable fashion) into the nucleus. In addition, the signal sequences of the present invention may be used to regulate the nuclear translocation of proteins that endogenously comprise such nuclear translocation signals.

The principles and operation of the nuclear localization signal according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The ability to regulate the cellular localization of a biological component is important for many functions such as the regulation of nucleic acid expression, transfection of eukaryotic cells, gene therapy, protection from toxic chemicals and transport of anti-cancer agents.

Figure 4A:
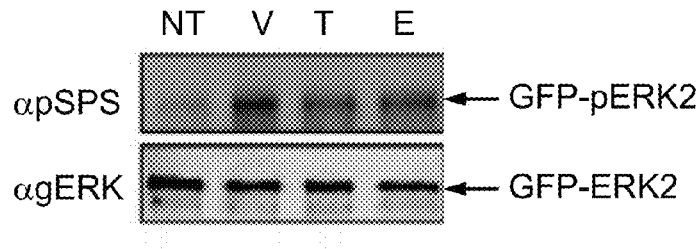
FIGS. 4A-I are autoradiographs characterizing SPS phosphorylation using an Ab to the phosphorylated SPS domain.
Figure 4B:
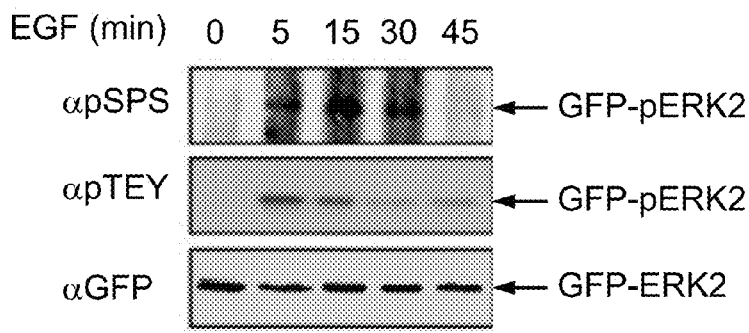

Through meticulous experimentation, the present inventors have identified a regulatory region, present in signaling proteins such as P42 MAP kinase (ERK2) protein, SMAD3 and mitogen-activated protein kinase kinase 1 (MEK1), that participates in nuclear translocation thereof upon extracellular stimulation. Deletion of this regulatory region prevented the nuclear accumulation of the proteins (FIGS. 1A-R and FIGS. 11A-E). The present inventors showed that upon stimulation of the cells with stimulators such as VOOH, TPA and EGF, the regulatory region undergoes phosphorylation and the attached protein translocates into the nucleus (FIGS. 2A-X; FIGS. 4A-B; and FIGS. 5A-F).

Whilst reducing the present invention to practice, the present inventors showed that this regulatory region may be linked to heterologous polypeptides, such as green fluorescent protein (GFP) to induce their nuclear translocation (FIGS. 8A-H and FIG. 9A), thereby demonstrating the generality and autonomous function of this regulatory region. Furthermore, the present inventors showed that mutation of the serine residues of this region to phosphomimetic residues induced an even higher level of nuclear translocation (FIG. 6; FIGS. 7A-H; FIGS. 8A-H and FIGS. 9A-B) of both naturally or synthetically linked polypeptide sequences.

In addition, the present inventors have shown that the above identified regulatory region behaves autonomously and may compete with endogenous signals (FIGS. 10M-X).

Furthermore, the present inventors have demonstrated that following phosphorylation of the regulatory region, the attached protein associates with importin-7 and is translocated into the nucleus (FIGS. 18A-G and 19A-C).

Thus, according to one aspect of the present invention, there is provided an isolated peptide comprising an amino acid sequence being no more than 19 amino acids in length, the amino acid sequence comprising:

$$X_1 \ X_2 \ X_3;$$ (SEQ ID NO: 1)

wherein $X_1$ and $X_3$ are each independently selected from the group consisting of serine, threonine, aspartic acid and glutamic acid;

wherein $X_2$ is proline, the isolated peptide comprising a nuclear targeting activity.

As used herein, the phrase "nuclear targeting activity" refers to the ability of the peptide to increase its nuclear:cytoplamic location ratio, or an agent linked thereto, by at least 10%, more preferably by at least 20% and even more preferably by at least 30%, 50%, 80% or more.

As mentioned above, the isolated peptide of the present invention may be any number of amino acids between 3 and 20. Exemplary isolated peptides of the present invention are set forth in SEQ ID NO: 2 and SEQ ID NO: 3.

Nuclear targeting activity can be detected by either direct or indirect means: Direct observation by fluorescence or confocal laser scanning microscopy is possible when the nuclear targeting peptide is labeled with a fluorescent dye (labeling kits are commercially available, e.g. from Pierce or Molecular Probes). Nuclear targeting activity can also be assessed by electron microscopy if the nuclear targeting peptide is labeled with an electron-dense material such as colloidal gold (Oliver, Methods Mol. Biol. 115 (1999), 341-345).

It will be appreciated that if the nuclear targeting peptide is linked to a heterologous agent (e.g. a polynucleotide), then the activity may be detected by observing the location of the heterologous agent.

Nuclear targeting activity can be assessed in indirect ways if the linked molecule (e.g. nucleic acid) exerts a function in the nucleus. This function can be, for example, the expression of a gene encoded by the linked nucleic acid including the consequences of such gene expression that may be exerted on other cellular molecules or processes.

Without being bound to theory, the present inventors believe that a peptide comprising an amino acid sequence serine/threonine, proline, serine/threonine (S/T-P-S/T) is a target for phosphorylation resulting in an incorporation of negative charges to an otherwise uncharged domain, which in turn acts as a signal to allow the peptide to cross the nuclear membrane.

Thus, according to this aspect of the present invention, when the peptide comprises serine or threonine in the place of $X_1$ or $X_3$, the nuclear targeting activity is regulatable. Conversely, when the peptide comprises phosphomimetic residues such as aspartic acid or glutamic acid in the place of $X_1$ or $X_3$, the nuclear targeting activity is typically constitutive. It will be appreciated that the peptide of the present invention may also comprise a serine or threonine as $X_1$ and an aspartic acid or glutamic acid as $X_3$, or vica versa. In such as case, the peptide location according to this embodiment may be only partially regulatable.

The term "peptide" or "polypeptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the peptides even more stable while in a body or more capable of penetrating into cells.

Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |

TABLE 2-continued

| Non-conventional amino acid | Code | Non-conventional amino acid | Code |
|---|---|---|---|
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |

TABLE 2-continued

| Non-conventional amino acid | Code | Non-conventional amino acid | Code |
|---|---|---|---|
| L-α ethylvaline | Mtrp | L-α-methyltyrosine | Mtyr |
| L-α-methylleucine | Mvalnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl-ethylamino)cyclopropane | Nmbc | | |

The peptides of the present invention may comprise leader sequences to modulate secretion thereof in the cell. An exemplary leader sequence may comprise myristic acid or the TAT-leader sequence as set forth in SEQ ID NO: 27.

The peptides of the present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides and/or polypeptides of the present invention. These techniques may be preferred when the peptide is linked to a heterologous protein (i.e. a fusion protein) since recombinant techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Examples of heterologous proteins are provided hereinbelow.

To produce a peptide and/or polypeptide of the present invention using recombinant technology, a polynucleotide encoding the nuclear targeting peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

As mentioned hereinabove, polynucleotide sequences of the present invention are inserted into expression vectors (i.e., a nucleic acid construct) to enable expression of the recombinant peptide. The expression vector of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals). It will be appreciated that the expression vector may also comprise polynucleotide sequences encoding other polypeptides that are transcriptionally linked to the nuclear targeting peptides of the present invention. Such polypeptides are further described herein below.

A variety of prokaryotic or eukaryotic cells can be used as host-expression systems to express the peptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

It will be appreciated that the polynucleotides of the present invention may also be expressed directly in the subject (i.e. in vivo gene therapy) or may be expressed ex vivo in a cell system (autologous or non-autologous) and then administered to the subject. Gene therapy techniques are further described hereinbelow.

Other than containing the necessary elements for the transcription and translation of the inserted coding sequence (encoding the polypeptide), the expression construct of the present invention can also include sequences engineered to optimize stability, production, purification, yield or activity of the expressed peptide.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant peptides and/or polypeptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant peptide and/or polypeptide is effected.

The phrase "recovering the recombinant polypeptide" used herein refers to collecting the whole fermentation medium containing the polypeptide and need not imply additional steps of separation or purification.

Thus, peptides and/or polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The peptides and/or polypeptides of the present invention are preferably retrieved in "substantially pure" form.

As used herein, the phrase "substantially pure" refers to a purity that allows for the effective use of the protein in the applications described herein.

In addition to being synthesizable in host cells, the peptide and/or polypeptide of the present invention can also be synthesized using in vitro expression systems. These methods are well known in the art and the components of the system are commercially available.

As mentioned hereinabove, the polynucleotides of the present invention may also be administered directly into a subject where it is translated in the target cells i.e. gene therapy.

Gene therapy as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ. The cells may be autologous or non-autologous to the subject. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

In in vivo gene therapy, target cells are not removed from the subject, rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.).

These genetically altered cells have been shown to express the transfected genetic material in situ.

To confer specificity, preferably the nucleic acid constructs used to express the peptides and/or polypeptides of the present invention comprise cell-specific promoter sequence elements, such as cancer specific promoters (e.g. survivin promoter—Chen et al, Cancer Gene Therapy, 2004, Volume 11, Number 11, Pages 740-747).

For gene therapy, nucleic acids are typically introduced into cells by infection with viral agents. This is because higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As mentioned hereinabove, nuclear targeting peptides of the present invention may be used to modulate nuclear translocation of both endogenous and exogenous polypeptides in host cells, including dividing (e.g. cell lines) and non-dividing cells (e.g. primary cells) and eukaryotic cells such as mammalian cells and yeast cells.

For example, the present inventors have shown that the nuclear targeting peptides of the present invention behave autonomously and compete with endogenous signals, such as those comprised in ERK. This results in down-regulation of the nuclear translocation of such endogenous signals.

Exemplary peptides that are capable of down-regulating endogenous polypeptides comprise amino acid sequence at least 70% homologous to a sequence as set forth by:

(SEQ ID NO: 4)
L D Q L N H I L G I L G $X_1$ P $X_2$ Q E D;

wherein $X_1$ and $X_2$ are any amino acid.

As used herein, the term "ERK" refers to the polypeptide "Extracellular-signal-regulated kinase" that translocates to the nucleus upon cell stimulation.

The present inventors have shown that in order to prevent ERK nuclear translocation, preferably $X_1$ and $X_2$ are non-phosphorylatable amino acids. Accordingly, preferably the amino acids do not comprise serine, threonine, aspartic acid or glutamic acid. According to one embodiment, the isolated peptide of this aspect of the present invention is as set forth in SEQ ID NO: 5.

It will be appreciated that the peptides of the present invention may also be able to prevent nuclear translocation of other polypeptides that endogenously comprise the presently identified signal peptides and down-regulate nuclear activities thereof in host cells. Examples of polypeptides that endogenously comprise the identified signal peptides of the present invention include, but are not limited to MEK SMAD, AKT and BRCA.

Since the peptides of the present invention are able to specifically inhibit the nuclear activities of ERK without modulating its cytoplasmic activities, these peptides may be used to inhibit ERK nuclear activities (e.g. proliferation) without harming other ERK-related cytoplasmic activities in the cells. Therefore, the peptides of this aspect of the present invention may serve as therapeutic agent for hyperproliferative diseases such as cancer without having the side-effects of other ERK inhibitors.

As mentioned, the present inventors have shown that following phosphorylation of the above identified polypeptides on their target phosphorylation sites (S/T-P-S/T), these polypeptides associate with importin-7 and are then translocated into the nucleus.

It will be appreciated therefore that, decreasing the activity or amount of importin-7 in a cell would down-regulate the amount of these polypeptides being translocated into the nucleus. As such, agents capable of down-regulating the activity/or amount of importin-7 are also contemplated as therapeutic agent for hyperproliferative diseases.

Thus according to another aspect of the present invention, there is provided a method of treating a hyperproliferative disease such as cancer in a subject.

As used herein the term "treating" refers to preventing, alleviating or diminishing a symptom associated with a hyperproliferative disease. Preferably, treating cures, e.g., substantially eliminates, the symptoms associated with the hyperproliferative disease.

Hyperproliferative conditions that can be treated according to the present invention are, but not limited to, brain, skin (such as melanoma), bladder, gastric, pancreatic, breast, head, neck, oesophageal, prostate, colorectal, lung, renal, gynaecological (such as ovarian) or thyroid cancer; other epitheliomas; cysts in various organs; warts and wart-like tumours induced by virus infection; fibrosarcoma and its metastases. In another embodiment, the present invention relates to treatment of non-cancerous hyperproliferative disorder, such as benign hyperplasia of skin or prostate (e.g. benign prostatic hypertrophy), synovial hyperplasia in rheumatoid arthritis, inflammatory bowel disease, restenosis, atherosclerosis, thrombosis, scleroderma or fibrosis.

According to one embodiment of this aspect of the present invention, the agent used to treat hyperproliferative disorders is a peptide agent as set forth in SEQ ID NO: 5.

According to another embodiment of this aspect of the present invention, the agent used to treat hyperproliferative disorders is an agent capable of down-regualting an activity and/or amount of importin-7.

As used herein, the term "importin-7" refers to the mammalian (e.g. human) importin-7 polypeptide capable of passing through the nuclear pore and being involved in nuclear transport. An exemplary importin-7 polypeptide sequence is set forth in NP_006382.

The agents capable of down-regulating importin-7 may be nucleic acid agents, such as siRNAs, RNAzymes, DNAzymes or antisense polynucleotides.

The term "siRNA" as used herein, refers to small interfering RNAs, which also include short hairpin RNA (shRNA) [Paddison et al., Genes & Dev. 16: 948-958, 2002], that are capable of causing interference and can cause post-transcriptional silencing of specific genes in cells, for example, mammalian cells (including human cells) and in the body, for example, mammalian bodies (including humans).

RNA interference is a two step process. The first step, which is termed the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr Opin Genetics and Development 12:225-232 (2002); and Bernstein, Nature 409:363-366 (2001)].

In the effector step, the siRNA duplexes bind to a nuclease complex from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr Op Gen Develop. 12:225-232 (2002); Hammond et al., 2001. Nat Rev Gen. 2:110-119 (2001); and Sharp Genes Dev. 15:485-90 (2001)]. Although the mechanism of cleavage is still to be elucidated, research indicates that each RISC contains a single siRNA and an RNase [Hutvagner and Zamore, Curr Opin Gen. Develop. 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al., Nat Rev Gen. 2:110-119 (2001), Sharp Genes Dev. 15:485-90 (2001); Hutvagner and Zamore Curr Opin Gen. Develop. 12:225-232 (2002)]. Ample guidance for using RNAi to practice the present invention is provided in the literature of the art [refer, for example, to: Tuschl, ChemBiochem. 2:239-245 (2001) incorporated herein by reference; Cullen, Nat Immunol. 3:597-599 (2002) incorporated herein by reference; and Brantl, Biochem Biophys Acta 1575:15-25 (2002) incorporated herein by reference].

Synthesis of RNAi molecules suitable for use with the present invention can be effected as follows. First, the mRNA sequence encoding the polypeptide of the present invention is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs), being enriched in regulatory protein binding sites. UTR-binding proteins and/or translation initiation complexes may interfere with binding of the siRNA endonuclease complex [Tuschl, Chem. Biochem. 2:239-245]. It will be appreciated though, that siRNAs directed at untranslated regions may also be effective, as demonstrated for GAPDH wherein siRNA directed at the 5' UTR mediated approximately 90% decrease in cellular GAPDH mRNA and completely abolished protein level (http://www.ambion.com/techlib/tn/142/3.html or http://www.ambion.com/techlib/tn/131/4.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Exemplary siRNAs capable of downregulating mammalian importin-7 are set forth in SEQ ID NOs: 28-32. Another exemplary siRNA capable of down-regulating mammalian importin 7 is disclosed in Saijou et al [J. Biol. Chem., Vol. 282, Issue 44, 32327-32337, Nov. 2, 2007].

Another agent capable of inhibiting importin-7 is an antisense polynucleotide capable of specifically hybridizing with an importin-7 mRNA transcript.

Design of antisense molecules which can be used to efficiently down-regulate the system output protein must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

The current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating importin-7 is a ribozyme molecule. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

As well as nucleic acid agents, the present invention also contemplates the use of antibodies or antibody fragments directed against importin-7 for the treatment of hyperproliferative disorders.

According to one embodiment, the antibody specifically binds at least one epitope of importin-7. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Another agent capable of down-regulating a function of importin-7 is a peptide agent capable of interfering with the binding of importin-7 to the ERK polypeptide. Since it was shown that importin-7 interacts with the phosphorylated "SPS" target site, the peptide capable of down-regulating a function of importin-7 may comprise these amino acids in order to compete with the endogenous "SPS" amino acids in ERK.

The present invention also anticipates preventing nuclear translocation of polypeptides that endogenously comprise the presently identified signal peptides by mutation of the identified sequences of the present invention by using knock-in strategies and the like.

Another means of modulating the nuclear translocation of endogenous polypeptides is by protein/protein interaction. Thus, for example, a nuclear targeting peptide linked to an antibody, may be introduced into a cell. The antibody recognizes and binds to its target polypeptide such that the target polypeptide becomes indirectly attached to the nuclear targeting peptide.

It will be appreciated that as well as functioning to modulate translocation of endogenous polypeptides, the peptides of the present invention may be linked to a heterologous substance via a linker, thereby acting as carriers, transporting the heterologous substance into the nucleus of a cell. It will be appreciated that the nuclear targeting peptide of the present invention may also attach to a heterologous substance in the cell and not in vitro. Thus the heterologous substance may be administered to the cell either prior to, concomitant with or following administration of the nuclear targeting peptide.

The heterologous substance may be any material which targeting thereof to the nucleus may be desired e.g. a pharmaceutical agent such as a therapeutic agent, a diagnostic agent or a cosmetic agent. Thus, according to this aspect of the present invention, the heterologous substance may be a polypeptide, a polynucleotide, a lipid, a carbohydrate, a hormone, a steroid, a small chemical, a virus and any combination thereof and the like.

According to an embodiment of this aspect of the present invention, the heterologous substance is a polypeptide. The polypeptide can be, for example, an immortalization protein (e.g., SV40 large T antigen and telomerase), an anti-apoptotic protein (e.g., mutant p53 and Bcl.sub.xL), an antibody, an oncogene (e.g., ras, myc, HPV E6/E7, and Adenovirus E1a), a cell cycle regulatory protein (e.g., cyclin and cyclin-dependent kinase), or an enzyme (e.g., green fluorescent protein, beta.-galactosidase, and chloramphenicol acetyl transferase).

According to another embodiment of this aspect of the present invention, the heterologous substance is a nucleic acid. The nucleic acid can be, e.g., RNA, DNA, or cDNA. The sequence of the nucleic acid can be a coding or a non-coding sequence (e.g., an antisense oligonucleotide).

The ability to safely and efficiently transfer nucleic acids into cells is a fundamental goal in biotechnology. Current synthetic synthetic delivery systems, although safe, are relatively inefficient. One of the major obstacles to efficient gene-delivery is targeting the genetic material into the nucleus. In current gene delivery methods, movement of DNA through the cytosol toward the nucleus occurs via diffusion, a relatively slow process during which the genetic material is exposed to a degrading cytoplasmic environment. Upregulating the efficiency of nuclear translocation of nucleic acids by incorporation of nuclear targeting peptides has already been accomplished—see for example Zanta et al., PNAS, Vol. 96, Issue 1, 91-96, Jan. 5, 1999; Subramanian, A. et al., (1999) Nat. Biotechnol. 17:873-877.

Thus the present inventors envision that the nuclear targeting peptides of the present invention will increase efficiency of various transfection protocols, including but not limited microinjection, electroporation, calcium phosphate coprecipitation, DEAE dextran introduction, liposome mediated introduction, viral mediated introduction, naked DNA injection, and biolistic bombardment.

According to yet another embodiment of this aspect of the present invention, the heterologous substance is a virus. The virus can be a whole virus or a virus core containing viral nucleic acid (i.e., packaged viral nucleic acid in the absence of a viral envelope). Examples of viruses and virus cores that can be transported include, but are not limited to, papilloma virus, adenovirus, baculovirus, retrovirus core, and Semliki virus core.

According to still another embodiment of this aspect of the present invention, the heterologous substance is a small molecule. The small molecule may be, for example a radionuclide, a fluorescent marker, or a dye.

According to an additional embodiment of this aspect of the present invention, the heterologous substance is a drug delivery system such as, e.g. magnetic particles, silica beads, PLGA, nano- or microspheres, chitosan etc.

According to yet another embodiment of this aspect of the present invention, the heterologous substance is an affinity moiety, such as an antibody, a receptor ligand or a carbohydrate. Linking of affinity moieties to the nuclear targeting peptides of the present invention is particularly beneficial when it is desirable to target a particular cell type with the nuclear targeting peptide. Examples of antibodies which may be used according to this aspect of the present invention include but are not limited to tumor antibodies, anti CD20 antibodies and anti-IL 2R alpha antibodies. Exemplary receptors include, but are not limited to folate receptors and EGF receptors. An exemplary carbohydrate which may be used according to this aspect of the present invention is lectin.

According to yet another embodiment of this aspect of the present invention, the heterologous substance is a detectable moiety.

The detectable moiety may be directly detectable typically by virtue of its emission of radiation of a particular wavelength (e.g. a fluorescent agent, phosphorescent agent or a chemiluminescent agent). Alternatively, the detectable moiety may be non-directly detectable. For example, the detectable agent moiety be a substrate for an enzymatic reaction which is capable of generating a detectable product.

It will be appreciated that the nuclear targeting peptides of the present invention may be linked to more than one heterologous substance either directly and/or indirectly.

The heterologous substance may be linked to the nuclear targeting peptide of the present invention by any method known in the art and which is appropriate for that particular heterologous substance. Thus for example, if the heterologous substance is a polypeptide, the linker may comprise a peptide bond or a substitiuted peptide bond, as described hereinabove. If the heterologous substance is a small molecule, the linker may comprise a non-peptide bond.

Examples of linking methods include, but are not limited to, chemical cross-linking, genetic fusion, and bridging.

Chemical Cross-Linking: Either a homobifunctional cross-linker or a heterobifunctional cross-linker can be used to cross-link a nuclear targeting peptide of the present invention with a heterologous substance. The homobifunctional or heterobifunctional cross-linker can be cleavable to facilitate separation of the nuclear targeting peptide from the heterologous substance after the nuclear targeting peptide transports the heterologous substance across a cell membrane. Homobifunctional cross-linkers have at least two identical reactive groups. Use of homobifunctional cross-linking agents may result in self-conjugation, intramolecular cross-linking and/or polymerization. Homobifunctional cross-linkers primarily are primary amine-reactive (e.g., imidoesters, N-succinimidyl esters, isothiocynates, carboxylic acids, and sulfonyl chlorides) or sulfhydryl reactive (e.g., 2-pyridyldithio, 3-nitro-2-pyridyldithio, maleimide, vinyl sulfone, aryl halide, dinitrofluorobenzene, organomercurial, p-chloromercuribenzoate, bismaleimidohexane, 1,5-difluoro-2,4-dinitrobenzene, and 1,4-di-(3'-(2'-pyrioyldithio)-propionamido) butane). Examples of homobifunctional imidoesters include, but are not limited to dimethyladipimidate, dimethylsuberimidate, and dithiobispropionimidate. Examples of homobifunctional NHS esters include, but are not limited to, disuccinimidyl glutarate, disuccinimidyl suberate, bis (sulfosuccinimidyl) suberate, dithiobis(succinimidyl propionate), and disuccinimidyl tartarate.

Heterobifunctional cross-linkers possess two or more different reactive groups that allow for sequential conjugation with specific groups, thus minimizing undesirable polymerization or self conjugation. Some heterobifunctional cross-linkers are amine reactive at one end and sulfhydryl reactive at the other end. Examples of such cross-linking agents include, but are not limited to, succinimidyl 4-(N-maleimidomethyl) cyclohexane-1-carboxylate, m-maleimidobenzyl-N-hydroxysuccinimide ester, succinimidyl 4-(p-maleimidophenyl)-butyrate, bismaleimidohexane, and N-(g-maleimidobutyryloxy) succinimide ester.

The homobifunctional or heterobifunctional cross-linking reactions can be stopped after adding linking the homobifunctional or heterobifunctional cross linker to the nuclear targeting peptide. The nuclear targeting peptide with a homobifunctional or heterobifunctional cross-linking agent can be purified by methods well known in the art and used as a stock for adding heterologous substances. Such purified nuclear targeting peptides with the attached homobifunctional or heterobifunctional cross-linking reagent can be stored, for example at −20° C. in aliquots and subsequently thawed. Once thawed a heterologous substance can be added by completing the cross-linking reaction.

Genetic Fusion: Genetic fusions can be generated by linking a coding sequence for a nuclear targeting peptide in-frame with a coding sequence for a polypeptide heterologous substance. Many methods exist in the art for linking coding sequences together. Exemplary methods include, but are not limited to, polymerase chain reaction (PCR), stitch PCR, and restriction endonuclease digestion and ligation. Preferably the reading frames of the nuclear targeting peptide and the heterologous substance are in frame and transcriptionally fused.

A protease cleavage site can be included between the nuclear targeting peptide and the polypeptide heterologous substance. Examples of such protease cleavage sites include, but are not limited to Factor Xa and tobacco etch virus (TEV) protease.

Bridging Molecules: Nuclear targeting peptides and heterologous substances can be complexed using pairs of bridging molecules. Examples of such pairs include, but are not limited to, (a) streptavidin and biotin, (b) glutathione and glutathione-S-transferase, and (c) polyhistidine and an affinity chromatography reagent (e.g., tetradentate nitrilotriacetic acid (NTA) or iminodiacetic acid (IDA)), which interact through an ion such as $Ni^{+2}$. A nuclear targeting peptide can be linked to either member of the pair, and a heterologous is linked to the other bridging molecule. For example, if the nuclear targeting peptide is linked to glutathione-S-transferase then the cargo is linked to glutathione. Alternatively, the nuclear targeting peptide may be linked to streptavidin and the heterologous substance may be linked to biotin. The nuclear targeting peptide and the streptavidin can be linked by any method known in the art for linking a peptide and a bridging molecule. Examples of such methods include, but are not limited to, chemical cross-linking or genetic fusion. The heterologous substance is then linked to biotin by any method known in the art for biotinylating small molecules, proteins, or nucleic acids, such as chemical cross-linking. The nuclear targeting peptide/heterologous substance complex can be formed by contacting the nuclear targeting peptide-streptavidin with the biotinylated heterologous substance.

A nuclear targeting peptide and heterologous substance can be complexed chemically or using pairs of bridging molecules at any position on either the nuclear targeting peptide or the heterologous substance, providing that functionality of either the nuclear targeting peptide or heterologous substance is not destroyed. For example, a cross-linking agent will react with appropriate functional groups located at the amino-terminus or carboxy-terminus (for proteins), at the 5' end or 3' end (for nucleic acids), or throughout the molecule.

A skilled artisan will be able to determine if the respective parts of the nuclear targeting peptide/heterologous substance complex retains biological activity. The nuclear targeting peptide retains biological activity if it can translocate the linked heterologous substance into a cell nucleus. Transport activity can be ascertained, for example, by adding the nuclear targeting peptide/heterologous substance complex to cells and assaying the cells to determine if the heterologous substance was delivered across into the nucleus using methods known in the art such as immunohistochemical staining. The heterologous substance can be assayed for activity using a method acceptable for the type of heterologous substance (e.g., an enzyme assay for an enzyme, a transformation assay for an oncoprotein, an anti-apoptotic assay for an anti-apoptosis protein, and an immortalization assay for an immortalization protein). These assays are well known in the art and are described in Sambrook et al., 1989 and Ausubel et al., 1989.

If the nuclear targeting peptide and polypeptide heterologous substance are genetically linked, the polypeptide cargo moiety can be complexed to either the amino terminus of the nuclear targeting peptide or to the carboxy-terminus of the nuclear targeting peptide. Preferably, the polypeptide cargo moiety is complexed to the N terminus of the nuclear targeting peptide of the nuclear targeting peptide.

As mentioned hereinabove, the present inventors have shown that the nuclear targeting peptides of the present invention must comprise a phosphorylated serine or thereonine in positions $X_1$ and $X_3$ of the amino acid sequence or alternatively phosphomimetic amino acids in these positions such as glutamic acid and aspartic acid in order for it to comprise nuclear translocating capabilities.

It will be appreciated therefore, that if positions $X_1$ and $X_3$ comprise serine or threonine, the activity of the nuclear targeting peptides may be modulated. Thus, the activity of these nuclear targeting peptides may be up-regulated by serine and/or threonine kinases or down-regulated by phosphatases. Modulating the activity of the nuclear targeting peptides may be effected following their introduction into the cell. Alternatively or additionally, modulation may be effected concomitant with and/or prior to introduction.

Other agents capable of regulating the activity of the nuclear targeting peptides of the present invention are those that are capable of activating or inhibiting kinases and phosphatases further upstream. Examples of agents capable of activating ser/thr kinases include, but are not limited to TPA, VOOH, TGFβ and EGF.

It will be appreciated that other agents capable of modulating serine and/or threonine phosphorylation may be identified using the nuclear targeting peptide agents of the present invention. According to this aspect of the present invention, the nuclear targeting peptides are linked to a detectable moiety prior to introduction into a cell. A change in the location of the nuclear targeting peptide in the presence of the candidate agent relative to the location of the nuclear targeting peptide in the absence of the candidate agent indicates that the agent is capable of modulating serine and/or threonine phosphorylation.

The nuclear targeting peptides of the present invention may be administered to the cells per se or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the nuclear targeting peptides of the present invention either alone or linked to a heterologous agent, or polynucleotides encoding same, which are accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the preparation in a local rather than systemic manner, for example, via injection of the preparation directly into a specific region of a patient's body.

A recombinant vector can be administered in several ways. If vectors are used which comprise cell specific promoters, for example, the procedure can take advantage of their target specificity and consequently, do not have to be administered locally at the diseased site.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that the polypeptides and polynucleotides of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorpotaed by reference as if fully set forth herein. Other general references are provided throughout this document. The procedures therein are believed to be well known in the art and are provided for the convenience of the reader. All the information contained therein is incorporated herein by reference.

General Materials and Methods

Reagents: Tetradecanoyl phorbol acetate (TPA), EGF, Leptomycin B (LMB) and 4'6-diamino-2-phenylindole (DAPI) were obtains from Sigma (St Louis, Mich.). Secondary antibody (Ab) conjugates were from Jackson Immunoresearch (West Grove, Pa.). Anti c-Jun, Tubulin E-19, HA-prob Y11 Abs were acquires from Santa Cruz Biotechnology (CA), and green fluorescent protein (GFP) Ab from Roche Diagnostics GmbH (Mannheim, Germany). Abs to doubly TEY phosphorylated ERK1/2 (pTEY-ERK), general ERK (gERK), and FLAG were from Sigma Israel (Rehovot, Israel) that also produced and purified the anti phospho SPS-ERK Ab (pSPS-ERK).

Buffers: Buffer A: 50 mM β-glycerophosphate (pH 7.3), 1.5 mM EGTA, 1 mM EDTA, 1 mM dithiothreitol, and 0.1 mM sodium vanadate. Buffer H consisted of Buffer A plus 1 mM benzamidine, 10 µg/ml aprotinin, 10 µg/ml leupeptin, and 2 µg/ml pepstatin A. Radio-immunoprecipitation assay (RIPA) Buffer: 137 mM NaCl, 20 mM Tris (pH 7.4), 10% (vol/vol) glycerol, 1% Triton X-100, 0.5% (wt/vol) deoxycholate, 0.1% (wt/vol) SDS, 2 mM EDTA, 1 mM PMSF, and 20 µM leupeptin. Buffer LS (low-stringency buffer) consisted of 20 mM HEPES (pH 8.0), 2 mM $MgCl_2$, and 2 mM EGTA.

HNTG Buffer: 50 mM HEPES (pH 7.5), 150 mM NaCl, 0.1% Triton X-100 and 10% (vol/vol) Glycerol.

Cell Culture and Transfection: COS7 cells were grown in Dulbecco's modified Eagle's medium (DMEM) with 10% fetal bovine serum (FBS), and were transfected using the DEAE-dextran method as described [H. Jaaro, H. Rubinfeld, T. Hanoch, R. Seger, *Proc. Nall. Acad. Sci. USA* 94, 3742 (1997)]. CHO cells were grown in F12-DMEM and transfected by polyethylenimine (PEI) as described [Y. D. Shaul, R. Seger, *J Cell Biol* 172, 885 (Mar. 13, 2006)]. After transfection, the cells were washed and grown under their corresponding conditions. SiRNAs were transfected using oligofectamin (Dharmacon Inc., Lafayette, Colo. USA) according to the manufacturer instructions.

DNA Constructs and Mutations: GFP-ERK2 was prepared in pEGFP C1 (Clontech, Mountain View, Calif.) as described [H. Rubinfeld, T. Hanoch, R. Seger, *J. Biol. Chem.* 274, 30349 (1999)], and GFP-MEK1 was in pEGFP-N1 (Clontech, Z. Yao et al., *Oncogene* 20, 7588 (2001)). HA-MEK1 was prepared in pCMV-HA. GFP-MH2-SMAD3 and the full length FLAG-SMAD3 were kindly provided by Dr. Joan Massaguè (Mermorial Sloan-Kettering Cancer Center, NY). The 2GFP constructs were a gift from Dr. Atan Gross (Weizmann Institute of Science, Rehovot Israel). To the C terminus of the 2GFP construct a 19 amino acid stretch containing the SPS of ERK2 was fused (LDQLNHILGILGSPSQEDL (SEQ ID NO: 6), termed 2GFP-WT).

Point mutations were performed by site-directed mutagenesis kit (Stratagene, La Jolla, Calif.) and confirmed by nucleotide sequence. The mutations were: GFP-ERK244-6A (244-6A), GFP-ERK Δ244-6 (Δ244-6), GFP-ERK244/6A (ERK-AA), GFP-ERK244/6E (ERK-EE). The Ser residues in the SPS domain of the 2GFP-WT were mutated to Ala (2GFP-AA) or to Glu (2GFP-EE). Residues 426-428 of FLAG-SMAD3 (ML) were replaced with Ala (ML-AAA), and the same mutation was inserted to GFP-MH2 SMAD3 (MH2-AAA). Residues 426/428 of MH2-SAMD3 were replaced with Glu (MH2-EE). Residues 386-8 in GFP-MEK1 were replaced with either Ala (MEK-AAA) or residues 386 and 388 were replaced with Glu (MEK-EE). Table 3 hereinbelow summarizes the primers used for the constructs of the present invention.

TABLE 3

| Construct | sense | antisense |
|---|---|---|
| ERKAAA | CACATCCTGGGTATTCTT GGAGCTGCAGCACAGGAAGAT SEQ ID NO: 7 | ATCTTCCTGTGCTGCAGCT CCAAGAATACCCAGGATGTG SEQ ID NO: 8 |
| ERKAPA | CCTGGGTATTCTTGGAGCTC CAGCACAGGAAGAT SEQ ID NO: 9 | ATCTTCCTGTGCTGGAGCT CCAAGAATACCCAGG SEQ ID NO: 10 |
| ERKEPE | CATCCTGGGTATTCTTGGAG AGCCAGAACAGGAAGATCTG SEQ ID NO: 11 | CAGATCTTCCTGTTCTGGC TCTCCAAGAATACCCAGGA TG SEQ ID NO: 12 |
| SMAD AAA | GTCCTCACCCAGATGGGTGC TGCAGCCATCCGCTGTTCCAG SEQ ID NO: 13 | CTGGAACAGCGGATGGCTG CAGCACCCATCTGGGTGAG GAC SEQ ID NO: 14 |
| SMAD DPD | GTCCTCACCCAGATGGGCGA CCCAGACATCCGCTGTTG SEQ ID NO: 15 | CAACAGCGGATGTCTGGGT CGCCCATCTGGGTGAGGAC SEQ ID NO: 16 |
| MEK EPE | CAGCCCAGCGAACCAGAA CATGCTGCTGGCGTC SEQ ID NO: 17 | AGCATGTTCTGGTTCGCTG GGCTGGTTAAGGCC SEQ ID NO: 18 |
| MEK AAA | CCTTAACCAGCCCAGCGCA GCAGCCCATGCTGC SEQ ID NO: 19 | GCAGCATGGGCTGCTGCGC TGGGCTGGTTAAGG SEQ ID NO: 20 |
| GFPGFPSPS | TCGAGGCCACCATGCTTGAC CAGCTGAATCACATCCTGGG TATTCTTGGATCTCCATCACA GGAAGATCTGC SEQ ID NO: 21 | CAGATCTTCCTGTGATGGA GATCCAAGAATACCCAGGA TGTGATTCAGCTGGTCAAG CATGGTGGCC SEQ ID NO: 22 |
| GFPGFPAPA | TCGAGGCCACCATGCTTGACC AGCTGAATCACATCCTGGGTA TTCTTGGAGCTCCAGCACAGG AAGATCTGC SEQ ID NO: 23 | CAGATCTTCCTGAGCTGGT GCTCCAAGAATACCCAGGA TGTGATTCAGCTGGTCAAG CATGGTGGCC SEQ ID NO: 24 |
| GFPGFP EPE | TCGAGGCCACCATGCTTGACC AGCTGAATCACATCCTGGGTA TTCTTGGAGAGCCAGAGCAGG AAGATCTGC SEQ ID NO: 25 | AATTCGCAGATCTTCCTGC TCTGGCTCTCCAAGAATAC CCAGGATGTGATTCAGCTG GTCAAGCATGGTGGCC SEQ ID NO: 26 |

Si-RNA of importin-7 (SEQ ID NOs: 28-32) and control Si-RNA were purchased from Dharmacon Inc. (Lafayette, Colo. USA).

Preparation of Cell Cellular Extracts: Cells were grown to subconfluency and then serum starved (0.1% FBS) for 16 h. After stimulation, the cells were rinsed twice with ice-cold phosphate-buffered saline (PBS) and once with ice-cold buffer A. Cells were scraped into buffer H (0.5 ml/plate) and disrupted by sonication (two 7-s pulses of 50 W). The extracts were centrifuged (20,000×g, 15 min, 4° C.), and the supernatants containing cytoplasmic and nuclear proteins were further analyzed as described below [D. M. Aebersold et al., *Mol Cell Biol* 24, 10000 (2004)].

Western Blotting: Cell extract was collected as described above, and aliquots from each sample (20 µg) were separated by 10% SDS-PAGE followed by Western blotting with the appropriate antibodies. The blots were developed with alkaline phosphatase or horseradish peroxidase-conjugated anti-mouse, anti-rabbit and anti-goat Fab Abs.

Cellular Fractionation: Transfected COS7 cells were starved (0.1% FBS) for 16 h, after which they were washed with ice-cold PBS, suspended in ice-cold buffer H, and centrifuged (12,000×g, 5 min). Then, the nuclear and cytosolic fractions were isolated as described [H. Rubinfeld, T. Hanoch, R. Seger, J. Biol. Chem. 274, 30349 (1999)]. Briefly, the pellets were suspended in 0.1% NP-40 followed by centrifugation (12,000×g, 5 min). The supernatant, containing the cytosolic fraction, was boiled in sample buffer. The pellet was suspended in extraction buffer (420 mM Nacl, 50 mM (3-glycerophosphate, 0.5 mM $Na_3VO_4$, 1.5 mM $MgCl_2$, 0.2 mM EDTA, 1 mM DTT, 25% glycerol), incubate on ice for 10 min, sonicated (50 W, 2×7 sec), and centrifuged (12,000×g, 5 min). The supernatant, containing the nuclear fraction, was subjected to Western blot.

Immunoprecipitation. Cellular extracts of stimulated transfected cells, were incubated with anti-GFP antibody preconugated to A/G beads (Santa Cruz; (2 hr, 4° C.). Subsequently, the beads were washed twice with HNTG buffer and once with 0.5 M LiCl. The immunoprecipitates were subjected either to Western blotting as described above or to an in vitro phosphatase assay as described under Results.

Immunofluorescence Microscopy. Cells were fixed (30 min in 3% paraformaldehyde in PBS or 10 min with ice-cold methanol), followed by 5-min permeabilization with 0.2% Triton X-100 in PBS (23° C.). The fixed cells were sequentially incubated with the appropriate Abs (45 min) followed by rhodamine-conjugated secondary Abs (45 min) and DAPI. Slides were visualized using a fluorescence microscope (Nikon, Japan) at 400× magnifications.

Example 1

Identification of the SPS Domain and its Role in the Regulation of ERK2 Basal Nuclear Accumulation Although the regulation and underlying mechanism of ERKs nuclear translocation remains unclear, previous studies suggest a role for the kinase insert domain (KID; T. Lee et al., Mol Cell 14, 43 (2004)). A thorough mutagenesis of the KID revealed a three amino acids sequence, composed of residues Ser244, Pro245 and Ser 246 (SPS) to be a significant domain for ERKs nuclear localization. To examine the functionality of this region, these three residues were replaced with Ala (244-6A) or deleted (Δ244-6) and overexpressed in CHO cells and COS7 cells.
Results
Unlike the reported nuclear accumulation of GFP-ERK2 in CHO cells [H. Rubinfeld, T. Hanoch, R. Seger, $J. Biol. Chem.$ 274, 30349 (1999)], both mutants were localized primarily in the cytoplasm (FIGS. 1A-F). These results were validated using overexpression in COS7 cells (FIGS. 1G-L), which contain a much higher amount of ectopically expressed proteins, clearly implicating the SPS domain in the regulation of the subcellular localization of ERK2 in quiescent cells. Similar results with more cells are shown in FIG. 1M-R.

Example 2

Figure 3:
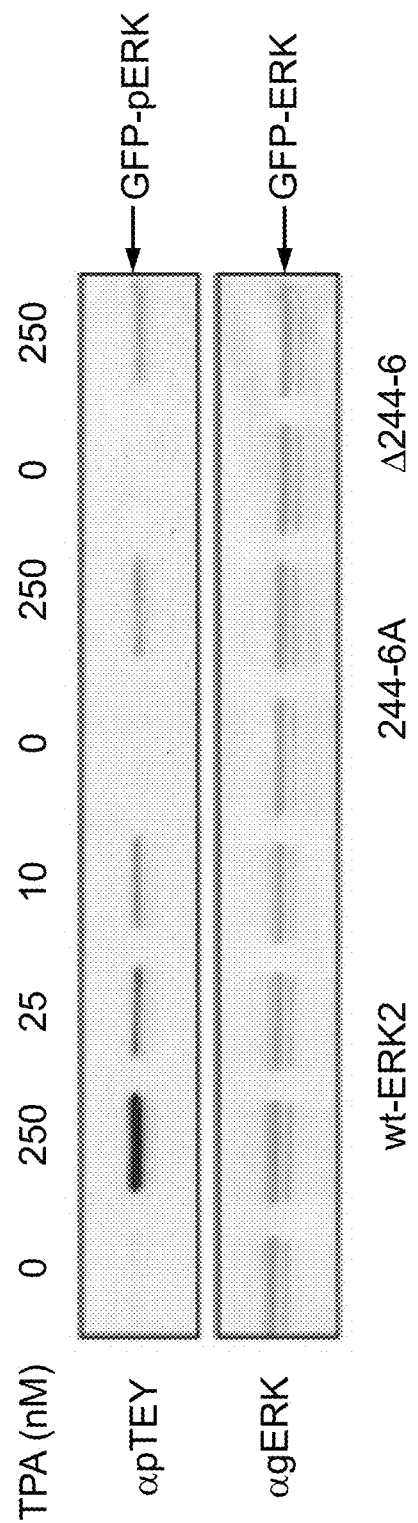
FIG. 3 is an autoradiograph illustrating the equilibration of ERK phosphorylation with different TPA concentration. ERK2 phosphorylation was detected by Western blot analysis using anti-phosphoTEY-ERK (αpTEY), and anti ERK Abs (αgERK).

The SPS Domain Plays a Role in the Nuclear Translocation of ERK2 Upon Stimulation Since the nuclear translocation of ERKs, is usually initiated in response to extracellular stimulation, the following experiments were performed in order to examine the role of the SPS domain in this stimulus dependent translocation as well. In order to follow ligand dependent cyto-nuclear ERK shuttling, the ERK constructs were cotransfected with MEK1, which acts as an anchoring protein, to secure cytoplasmic localization of ERKs in the basal state.
Results
As expected, the cotransfected WT-GFP-ERK2 [H. Rubinfeld, T. Hanoch, R. Seger, $J. Biol. Chem.$ 274, 30349 (1999)] was localized in the cytoplasm of the resting CHO cells, and translocated into the nucleus upon TPA stimulation (250 nM). However, the two SPS mutants remained localized in the cytoplasm irrespective of TPA stimulation (FIGS. 2A-X). A possible reason for this lack of translocation could be a reduced phosphorylation of the Thr and Tyr residues within the TEY motif of the mutants. Indeed the rate of phosphorylation of the mutants detected by anti pTEY-ERK antibody was lower than that of WT-ERK2 (FIG. 3) indicating that the SPS domain is involved in the phosphorylation of ERKs by mEKs. To determine whether the cytoplasmic retention of the SPS mutants after TPA stimulation is a result of reduced TEY phosphorylation but is inherent to the mutants, phosphorylation levels were equilibrated using different concentrations of TPA (10 nM for WT-ERK2 and 250 nM for the mutants, FIG. 3). Also with equivalent phosphorylation levels, WT-GFP-ERK2 is localized to the nucleus, whereas the SPS mutants remain restricted to the cytoplasm. The abrogation of facilitated nuclear translocation of the SPS mutants was also detected using different stimulants such as EGF and VOOH (data not shown). Therefore, these results indicate that the abrogated nuclear translocation is an intrinsic property of the mutants and not the result of a reduced TEY phosphorylation. This conclusion is further supported by the finding that 244-6A-ERK2 interacted with MEK1 and detached from it upon stimulation, similarly to WT-ERK2 (FIG. 3). Thus, the change that is induced by the SPS mutation partially affects only the phosphorylation by MEKs but not the binding or detachment, confirming that no major conformational changes are induced by the mutations. Therefore, the lack of nuclear accumulation of the SPS mutated ERK2 are probably due to other, inherent effect of this region. Taken together, these data implicate the SPS domain in the mediation of ERKs nuclear translocation, both in resting cells and upon extracellular stimulation.

Example 3

The Ser Residues in the SPS Domain are Phosphorylated Upon Cellular Stimulation

The following experiments were carried out in order to examine whether the serine residues within the novel translocation sequence comprise potential phosphorylation sites. Indeed, the sequence of the SPS domain and its surrounding residues (Gly-Ser-Pro-Ser-Gln-Glu-Asp—SEQ ID NO: 37) consist of several consensus phosphorylation sites for protein kinases, such as MAPKs, CDKs, CKII and ATM. Therefore, the possibility that the Ser residues within the SPS domain undergo an additional phosphorylation concomitantly with nuclear translocation was examined. Mass spectroscopic analysis was performed on GFP-ERK2 immunopreciptates extracted from stimulated or un-stimulated COS7 cells.
Results
It was found that in addition to a trypsin-digested peptide containing the phosphorylated TEY motif, a peptide corresponding to the SPS domain contained an incorporated phosphate. The SPS phosphorylated peptide was detected in the activated GFP-ERK2, but not in the protein derived from the non-stimulated cells (data not shown). Since the only phospho-acceptors in this peptide were the two Ser residues in the SPS, it is possible that the appearance of this peptide represents phosphorylation of a Ser residue within this domain.

Example 4

Characterization of SPS Phosphorylation by a Specific Antibody

Figure 4C:
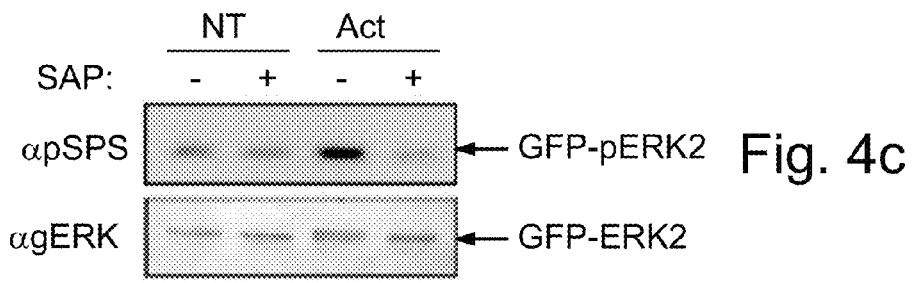
Figure 4D:
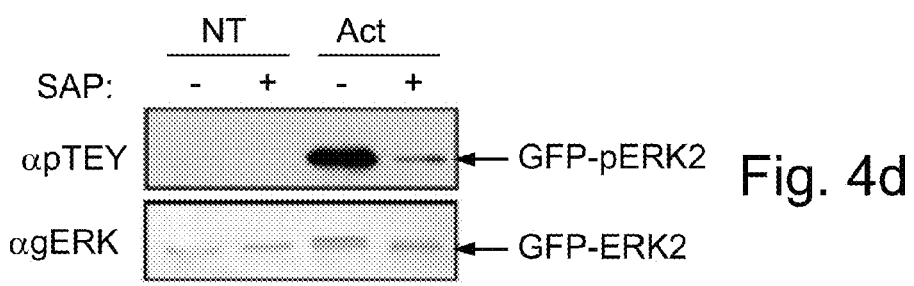
Figure 4E:
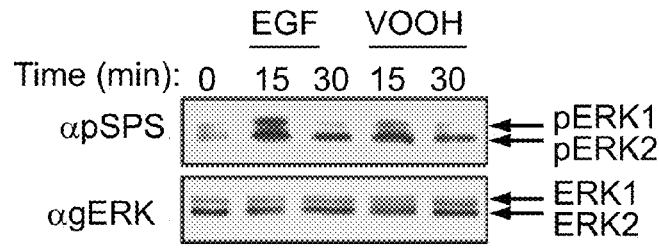
Figure 4F:
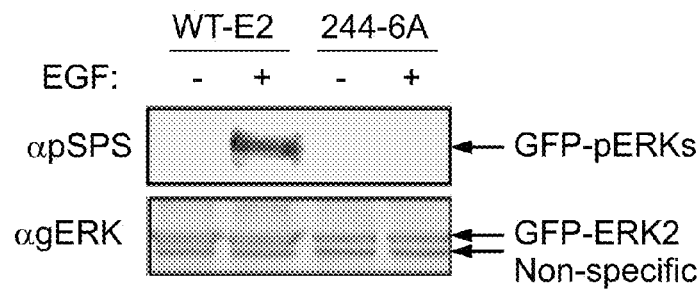

To further study the occurrence and role of SPS phosphorylation, a polyclonal antibody (Ab) directed against a doubly phosphorylated SPS peptide was raised. It is likely that such an Ab preparation will include Ab directed either against each monophosphorylated Ser or against the doubly phosphorylated Ser.
Results
In a Western blot, the antibody weakly recognized a 72 kDa band, corresponding to GFP-ERK2 immunoprecipitated from starved, transfected COS7 cells (FIG. 4A). This recognition of GFP-ERK2 was significantly increased when the GFP-ERK2 was immunoprecipitated from VOOH, TPA and EGF stimulated cells, suggesting that the SPS is phosphorylated upon stimulation. Indeed, time course of EGF stimulation revealed a transient increase in SPS phosphorylation, which peaked at 15 minutes following stimulation and a decrease thereafter (FIG. 4B). This time course was slower than TEY phosphorylation that peaked at 5 minutes following stimulation. This rate of SPS phosphorylation correlated better with translocation, suggesting sequential events in the activation of ERKs and their subsequent SPS-phosphorylation and translocation to the nucleus. Similar phosphorylation patterns detected by the Ab were also found with endogenous ERKs from EGF or VOOH stimulated cells (FIG. 4E).

Figure 4G:
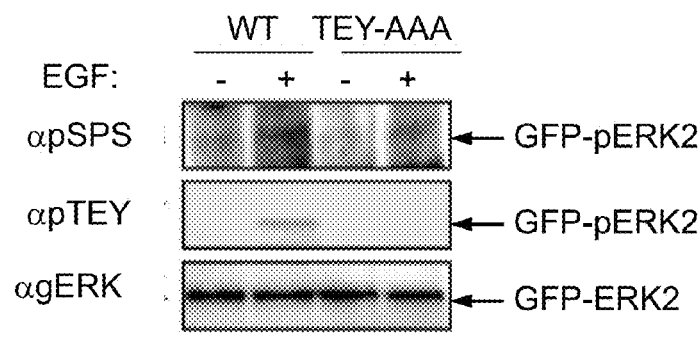

Treatment of the phosphorylated ERK2 with alkaline phosphatase demonstrated a significant reduction in the immunoreactivity of the anti phospho-SPS Ab (FIG. 4C) as well as the control anti phospho-TEY Ab (FIG. 4D), confirming the quality of the antibodies. The small reduction in immunoreactivity upon phosphatase treatment of non-stimulated ERK2 indicates that the amount of phosphorylated SPS-ERK2 in quiescent cells is low, and that the anti phosphoSPS antibody may recognize also a minute amount of non-phosphorylated ERK2. Finally, it was found that the TEY mutated ERK2 that does not contain phosphates in this site (TEY-AAA) can still be recognize by the anti phosphoSPS Ab upon stimulation (FIG. 4G) indicating again that the Ab is specific to the SPS phosphate and does not recognize any other incorporated phosphates of ERK2. Taken together, these results identify a novel stimulation-dependent phosphorylation of ERKs on their SPS domain.

Example 5

Phosphorylation of SPS is Mediated in Part by ERK Autophosphorylation

Figure 4H:
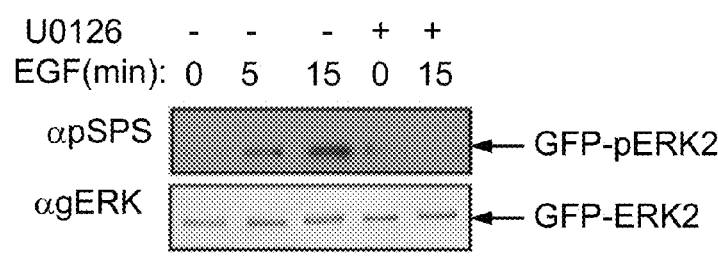
Figure 4I:
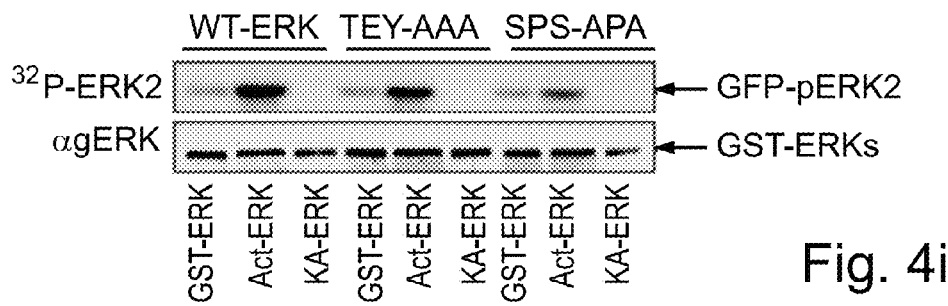

Since the SPS phosphorylation seems to correlate with the activation of the ERK cascade, the possibility that this phosphorylation is mediated by components of this cascade was examined. Because of the slower time course of phosphorylation (FIG. 4B), and because of the specificity of the upstream Raf kinases and MEKs that cannot phosphorylate this sequence (Yoon and Seger, 2006, Growth Factors, 24, 21-44), the possibility that the kinase(s) are localized downstream of MEKs was examined.
Results
The anti pSPS Ab, which detected GFP-ERK2 from EGF-stimulated cells, did not react with GFP-ERK2 immunoprecipitated from cells that were pretreated with the MEK inhibitor U0126 prior to stimulation (FIG. 4H). Some protein kinases downstream of MEKs that may be involved in the SPS phosphorylation are ERKs themselves (autophosphorylation) as their consensus phosphorylation site includes Ser/Thr followed by a Pro (Yoon and Seger, 2006, Growth Factors, 24, 21-44). Therefore, the present inventors examined whether the kinases involved in the phosphorylation are ERKs themselves. To this end, immunoprecipitated purified GFP-ERK2, as well as TEY-AAA-ERK2, and ERK2 in which the two Ser residues in the SPS sequence were replaced by Ala (SPS-APA) were used. These three proteins were subjected to in vitro phosphorylation by either a purified low activity GST-ERK2 (GST-ERK), active GST-ERK2 (Act-ERK) prepared from bacteria co-expressing active MEK1 (Jaaro et al., 1997, PNAS, 94, 3742-3747), and inactive GST-ERK2 in which the Lys in the ATP binding site was substituted with an Ala residue (KA-ERK). As expected, $^{32}$P incorporation to GFP-ERK2 was detected mainly when this protein was incubated with Act-ERK2. The phosphorylation of TEY-AAA was reduced by ~25%, while that of SPS-APA was reduced by ~80% (FIG. 4I). These results indicate that active ERKs can trans-autophosphorylate on the SPS domain. Thus, ERK2 and probably other kinases downstream of MEKs could be, at least in part, the kinases that phosphorylate the SPS domain upon stimulation.

Example 6

The Nuclear Translocation of ERKs is Mediated by SPS Phosphorylation

Both the phosphorylation on the SPS domain and the abrogation of nuclear translocation by the SPS mutants suggests that phosphorylation may be required for ERK2 stimulation dependent nuclear translocation. To further study this possibility, the two Ser residues were replaced in the SPS domain, either with Glu that acts as a phosphomimetic residue, or with Ala as control.
Results
GFP-EPE-ERK2 showed a pronounced nuclear localization, while the APA-mutant exhibited a cytoplasmic distribution similar to that of the 244-6A construct (FIGS. 5A-F and FIGS. 1M-R). These differences in distribution were confirmed by subcellular fractionation assay that showed that about 75% of WT-ERK2, 95% of EPE-ERK2 and only 5% of APA-ERK2 are localized in the nucleus 48 hr after transfection (FIG. 6). The difference between WT- and EPE-ERK2 was even more pronounced shortly after transfection (FIGS. 7A-H), indicating that EPE-ERK2 translocates into the nucleus faster than WT-ERK2. Therefore, these results indicate that indeed the SPS phosphorylation plays a role in facilitating the translocation of ERK2 into the nucleus. Similar results were obtained also upon treatment with leptomycine B (LMB) that prevents nuclear export (FIGS. 15A-R), indicating that SPS mutation modulate the nuclear import and not export of ERKs. In addition, the SPS-induced translocation seems to be important for the downstream activity of ERKs, as phospho-deficient mutants prevented serum-induced cell proliferation, while the phosphomimetic EPE-ERK2 slightly enhanced this process (FIG. 16).

Example 7

Use of a GFP Chimera to Study the Role of Phosphorylated SPS

Figure 9A:
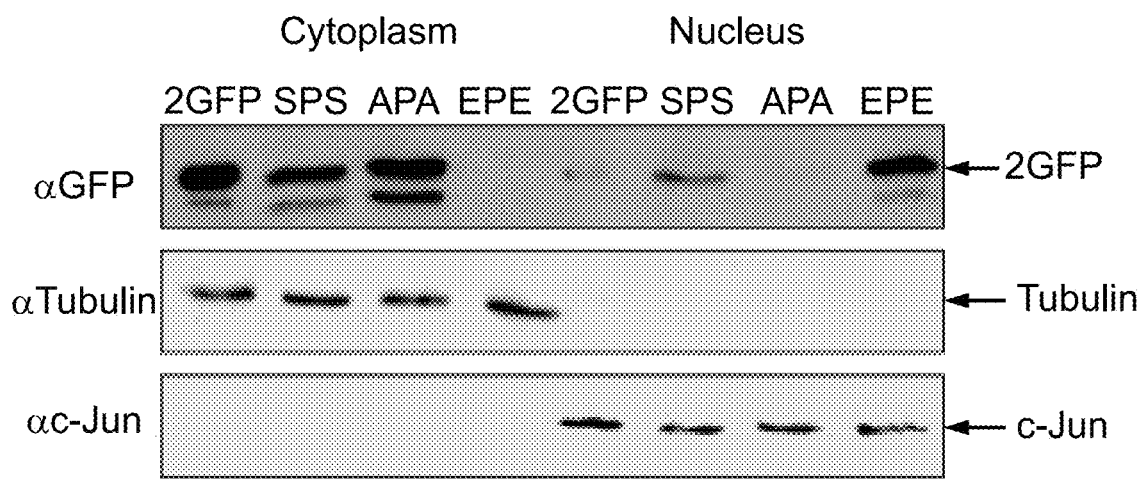
FIG. 9A is an autoradiograph illustrating the subcellular fractionation of transfected SPS, APA, and EPE peptides fused to a 2GFP in COS7 cells. Western blot analysis of aliquots of the fractions were stained with anti GFP Ab to detect the different chimaras, and with anti tubulin and anti c-Jun Abs as markers for the cytoplasmic and nuclear fractions respectively.
Figure 9B:
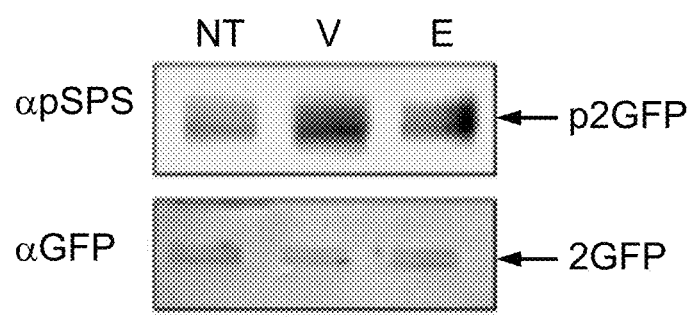
FIG. 9B is an autoradiograph illustrating that stimulation elevates pSPS phosphorylation of 2GFP-SPS construct. COS7 cells overexpressing 2GFP-SPS construct were serum starved followed by stimulation with VOOH (V, 100 μM $Na_3VO_4$ and 200 μM $H_2O_2$, 15 min), and EGF (E, 50 ng/ml, 15 min), or left untreated (NT). The 2GFP-SPS was immunoprecipitated with anti GFP Ab, extensively washed, and the immunoprecipitated proteins were subjected to WB using anti-pSPS Ab (αpSPS). The total amount of immunoprecipitated 2GFP-SPS was detected with αGFP Ab.

To validate the general importance of the SPS domain, a 19 amino acid sequence surroundings the SPS or the APA and EPE mutants was fused to a dimer of GFP proteins (2GFP). Cellular distribution of the chimeras was detected in CHO cells 24 hr post transfection of the GFP constructs.
Results
The 2GFP-SPS construct was localized throughout the cell, the 2GFP-APA appeared mainly in the cytoplasm and perinuclear region, and the 2GFP-EPE was detected mainly in the nucleus (FIGS. 8A-H). These results were confirmed by subcellular fractionation experiment that gave essentially similar results as the immunostaining experiments (5% 2GFP, 15% 2GFP-SPS, 3% 2GFP-APA and 90% 2GFP-EPE were localized in the nucleus; FIG. 9A). As expected, the SPS peptide in the 2GFP chimera was phoshorylated upon stimulation with EGF or VOOH (FIG. 9B), suggesting that SPS-kinase does not require ERK conformation for its action.

As demonstrated, the SPS domain functions autonomously, and may therefore compete with endogenous SPS signals. Indeed, the overexpressed cytoplasmic 2GFP-SPS and more so 2GFP-APA, but not the nuclear 2GFP-EPE, inhibited the TPA-induced translocation of endogenous ERKs (FIGS. 10M-X). The lack of the expected inhibitory 2GFP-EPE effect lies probably in its rapid nuclear accumulation, which prevents its possible influence on the cytoplasmic endogenous ERKs. Notably, none of the mutants had an effect on the localization of ERKs in resting cells (FIGS. 10A-L), indicating that the SPS domain competes with the translocation of endogenous ERKs only when phosphorylated. Thus the present findings implicate the phosphorylated SPS domain as a novel, general nuclear translocation signal (NTS).

Example 8

Phosphorylated SPS Domain Plays a Role in the Nuclear Translocation of SMAD3

The phosphorylated SPS-induced translocation of the inert protein 2GFP prompted the present inventors to further study the generality of this domain in the nuclear translocation of other signaling molecules. A sequence homology search revealed that SMAD3, a signaling protein that translocates into the nucleus upon TGF-β stimulation [J. Massague, S. W. Blain, R. S. Lo, Cell 103, 295 (Oct. 13, 2000), contains an SPS domain in the MH2 region (FIG. 20) that has previously been implicated in the nuclear translocation of the protein [L. Xu, C. Alarcon, S. Col, J. Massague, J Biol Chem 278, 42569 (Oct. 24, 2003)].

Results

The present inventors found that the TGFβ-induced nuclear translocation is mediated by importin-7, as knockdown of this protein prevented the translocation of the endogenous SMAD3 protein (FIG. 17A-B). Using anti pSPS Ab, it was found that WT-Flag-SMA3 is phosphorylated on its SPS domain upon stimulation with VOOH, TPA and TGFβ (FIG. 11E). Therefore, it seems likely that the SPS of SMAD3 operated similarly to that of ERK2. To examine whether this SPS of SMAD3 is involved in nuclear translocation WT-Flag-SMAD3 and a Flag-SMAD3 in which the SPS domain was replaced with three Ala residues (AAA-SMAD3) were overexpressed in CHO cells and their localization examined.

Similarly to ERK2, overexpression of the WT-Flag-SMAD3 resulted in its nuclear localization, while the mutant was found primarily in the cytoplasm (FIGS. 11A-D). For additional characterization of the SPS domain of SMAD3, a truncated form of the protein was used containing all the elements required for the proper subcellular localization of the protein (MH2, [L. Xu, C. Alarcon, S. Col, J. Massague, J Biol Chem 278, 42569 (Oct. 24, 2003)]), and, importantly also the SPS domain. The MH2 region was fused to GFP (WT-MH2), and the SPS domain was replaced either with three Ala (AAA-ML) or the two Ser residues with Asp (DPD-ML). Overexpression of the WT-MH2 resulted in a nuclear distribution, while the AAA-MH2 and DPD-MH2 were localized in the cytoplasm or the nucleus respectively, as detected by fluorescence microscopy (FIGS. 12A-F) or by fractionation studies in which 75% of WT-MH2, 7% of AAA-MH2 and 88% of DPD-MH2 were localized in the nucleus (FIG. 13). Thus, SMAD3, like ERK2 contains a phosphorylated SPS domain important for its nuclear translocation.

Example 9

Importin-7 Mediates the Stimulation-Dependent Nuclear Translocation of ERKs in a Ran-Dependent Manner The nuclear translocation of ERKs (Chen et al., 1992, Mol Cell Biol, 12, 915-927), can occur either by a passive diffusion or by an active transport (Adachi et al., 1999, EMBO J, 18, 5347-5358), which are governed by various distinct mechanisms (Yazicioglu et al., 2007, J Biol Chem). In Drosophila it was suggested that D -Importin-7 (DIM-7) is responsible for the accumulation of ERKs in the nucleus during development (Lorenzen et al., 2001, Development, 18, 1403-1414). Therefore, the present inventors examined whether the mammalian analogue of this protein plays a role in ERK translocation in mammals as well.

Results

Transfection of Si-RNA of mammalian importin7 to HeLa cells dramatically reduced EGF-induced translocation of ERK2, as compared to the translocation detected in cells transfected with control Si-RNA (FIG. 18A). On the other hand, the Si-RNA of importin-7 had only a small inhibitory effect on the passive nuclear accumulation of overexpressed WT-ERK2 (FIG. 18B). In both experiments, the cells transfected with Si-importin-7 lost considerable amount of importin-7, but not other proteins such as ERKs that served as a control (FIG. 18C). Moreover, it was found that importin-7 can interact with both overexpressed ERK2 (FIG. 18D) and endogenous ERKs (FIG. 18E), and the interaction was significantly increased upon stimulation with EGF. Therefore, these results indicate that importin-7 is an important regulator of the activation-induced, but much less passive, nuclear translocation of ERKs.

The possible involvement of the small GTPase Ran, an important regulator of nuclear transport was then examined. In NLS-dependent transport, Importin-α, binds its NLS-containing cargo in the cytoplasm, which contains primarily RanGDP, and after the transport through the nuclear pores releases the cargo in the nucleus upon binding of the nuclear RanGTP to the complex. Therefore the present inventors examined whether importin-7-ERK complex is also Ran-regulated by following the possible interactions between the components. Indeed, it was found that importin-7 specifically interacts with Ran-GTP, and not with Ran-GDP, or Ran without a loaded guanidine (NG; FIG. 18F). Moreover, the presence of Ran-GTP, but not Ran-GDP, caused dissociation of the importin7-ERK complex (FIG. 18G), indicating that importin-7-ERK complex is regulated by Ran-GTP similarly to complexes of the other importins. Taken together, these results suggest that the active nuclear translocation of ERKs is mediated by importin7, and that this process is regulated by Ran.

Example 10

Phosphorylated TPT Domain Plays a Role in the Nuclear Translocation of MEK1

Other proteins that translocate into the nucleus upon stimulation are the MEKs [H. Jaaro, H. Rubinfeld, T. Hanoch, R. Seger, Proc. Natl. Acad. Sci. USA 94, 3742 (1997)]. It was found that similarly to ERK2 and SMAd3, also MEK translocation into the nucleus was mediated, at least in part, by importin-7 (FIGS. 17A-B). Interestingly, MEKs do not contain an SPS domain, but rather have a TPT sequence next to a region that participates in the determination of their subcellular localization [H. Cha, E. K. Lee, P. Shapiro, J Biol Chem 276, 48494 (Dec. 21, 2001)]. This TPT sequence was also shown to be phosphorylated upon cellular stimulation [S. Matsuda, Y. Gotoh, E. Nishida, J Biol Chem 268, 3277 (Feb. 15, 1993)], and to be involved in protein-protein interaction that can determine subcellular localization [A. Nantel, K. Mohammad-Ali, J. Sherk, B. I. Posner, D. Y. Thomas, J Biol Chem 273, 10475 (Apr. 24, 1998). The following experiment was performed in order to examine whether the cyto-nuclear shuttling of MEKs requires the phosphorylation of this putative NTS. The two Thr residues within the TPT domain of MEK1-GFP were replaced with either Ala or Glu residues and their subcellular localization was followed upon overexpression in CHO cells.

Figure 14:
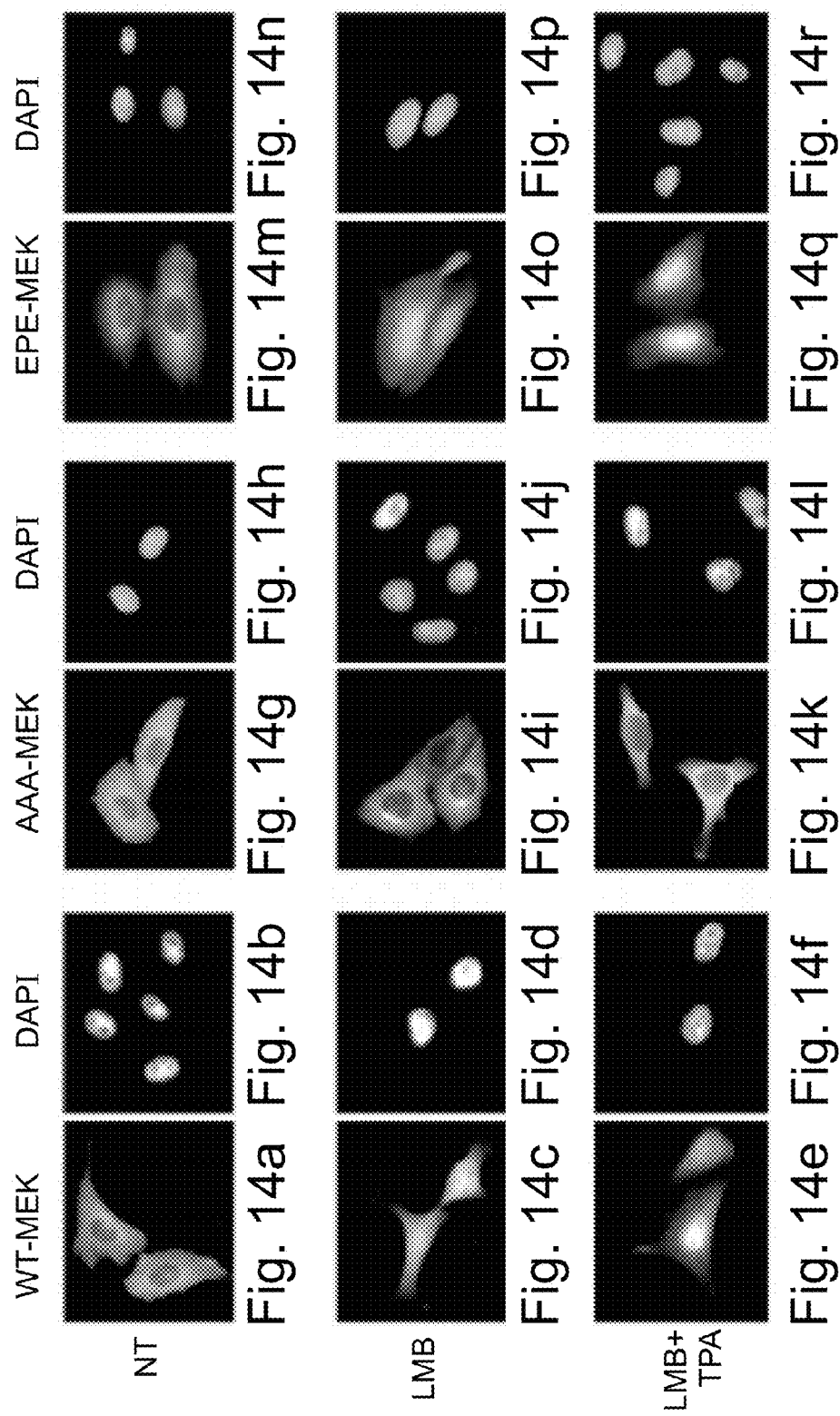
FIGS. 14A-R are photomicrographs illustrating that the NTS motif regulates MEK1 shuttling into the nucleus. CHO cells overexpressing WT-GFP-MEK1 (WT), AAA-GFP-MEK1 (AAA-MEK) and EPE-GFP-MEK1 (EPE-MEK) were starved for 16 hr and treated with LMB (5 ng/ml, 1 hr; LMB), LMB (5 ng/ml, 1 hr)+TPA (250 nM, 15 min; LMB+TPA) or left un treated (NT). Subsequently the cells were fixed, stained with DAPI and visualized by a fluorescent microscope.

As expected from the presence of a nuclear export signal (NES) in MEKs, WT -MEK1-GFP and the mutants were localized primarily in the cytoplasm of non-treated cells (FIGS. 14A-R). The addition of the exportin inhibitor leptomycin B (LMB, [Z. Yao et al., Oncogene 20, 7588 (2001)]) induced a moderate nuclear translocation of WT-MEK1, which was increased in the EPE-MEK1 and abrogated in the AAA-MEK1. Stimulation of the cells with TPA increased the nuclear accumulation of WT-MEK1-GFP but not that of the EPE-MEK1 that was localized in the nucleus even without stimulation. Importantly, the AAA-MEK1 was localized in the cytoplasm, confirming that like with ERK2, the TPT domain plays a role in the stimulated translocation and not only in the non-regulated shuttling of MEK1. Thus, in similarity to the SPS domains of ERK2 and SMAD3, the TPT domain mediates the nuclear translocation of MEK1.

Example 11

Phosphorylated SPS Domain is Required for ERK2 Interaction with Importin-7 and Release from Nuclear Pore Protein (NUPs)

The finding that importin-7 is involved in ERKs nuclear translocation prompted the present inventors to examine whether the phosphorylation of the SPS is required for this process. The possible involvement of importin-β, which seems to cooperate with importin-7 in some nuclear transport systems was also examined.

Results

Figure 19A:
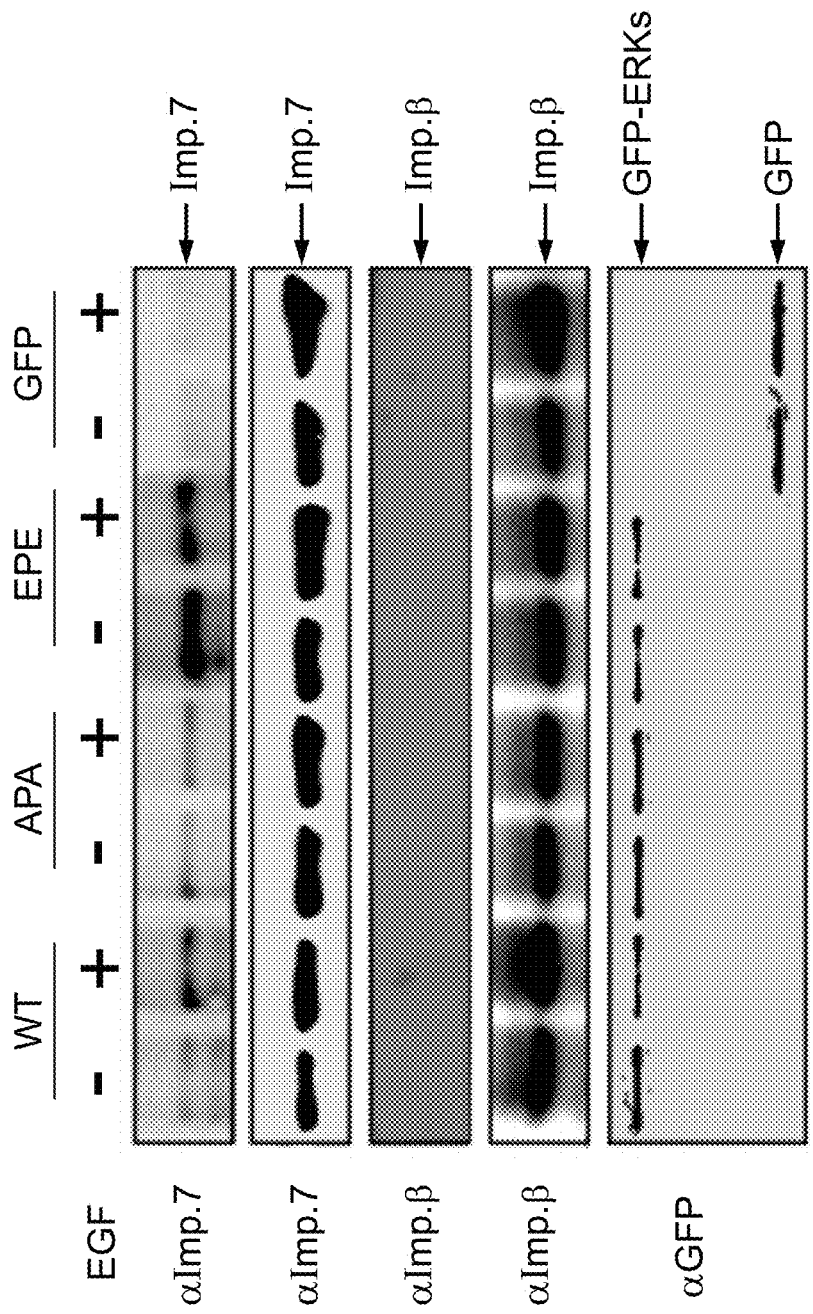
FIGS. 19A-C are autoradiographs illustrating that phospho-SPS interacts with importin-7 and releases Nup153c binding without involvement of importin-13.
Figure 19B:
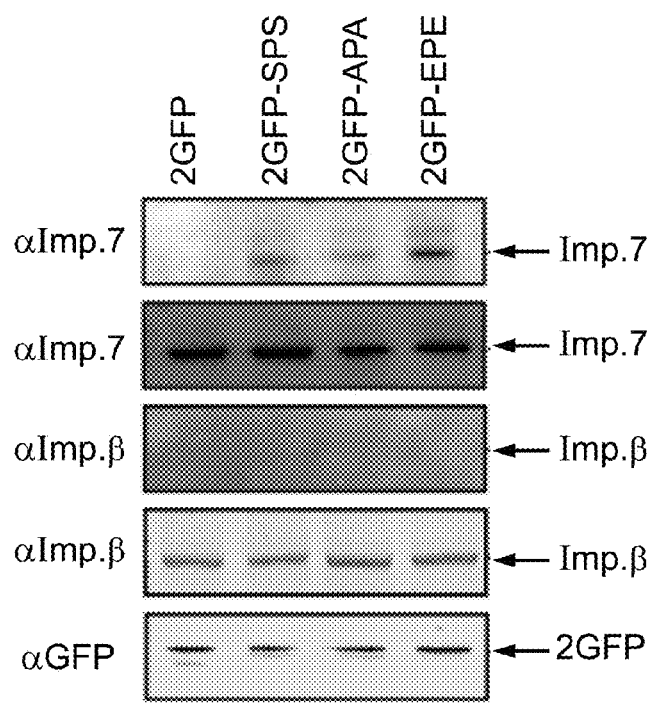

The interaction of the various SPS mutants with importin-7 and importin-β was examined. Co-immunoprecipitation experiments revealed that WT-ERK2-importin-7, interaction is significantly increased upon TPA stimulation (FIG. 19A). Prevention of SPS phosphorylation using APA mutation reduced the interaction, mainly upon stimulation, while the use of the phosphomimetic EPE mutation dramatically increased the interaction with or without stimulation. Similar results were obtained using the 2GFP constructs (FIG. 19B), as the SPS conjugated 2GFP did bind importin-7, the APA sequence reduced this interaction and the EPE elevated it. On the other hand, no interaction with importin-β was detected in the same experiments, indicating that this protein is not directly involved in the translocation, and supporting the specificity of the coimmunoprecipitation reaction. These results clearly demonstrate the involvement of the phosphorylated SPS in the stimulated, importin-7-dependent translocation of ERKs into the nucleus.

Another mechanism that was suggested to play a role in the nuclear translocation of ERKs is their direct interaction with NUPs. Examining this interaction in the present system revealed that indeed WT-ERK2 interacts with Nup153, and the interaction is slightly increased upon stimulation. Surprisingly, the interaction with NUP153 was increased, not decreased, with the APA mutant, while the interaction with EPE mutant was reduced. This result may indicate that the interaction with Nup153 is mediated mostly by other residues of ERK2, and the phospho-SPS is required for the release of ERKs from the NUPs, which consequently facilitates the nuclear translocation of ERKs. Therefore, the phosphorylation of the SPS domain seems to play a dual role in the nuclear transport: enhancing interaction with the adaptor importin-7 and expediting the release from NUPs.

CONCLUSIONS

Nuclear translocation of signaling molecules is crucial for their proper stimulus-dependent functioning in the regulation of cellular processes such as proliferation and differentiation. Interestingly, many of these proteins do not contain the canonical NLS, and their mechanism of nuclear translocation is not fully understood. The present inventors identified a novel sequence that seems to act as a general NTS in signaling proteins. The major role of the canonical and other rare NLSs [D. Christophe, C. Christophe-Hobertus, B. Pichon, Cell Signal 12, 337 (May, 2000)], is the nuclear shuttling of proteins that are constantly retained in the nucleus by virtue of their NLS-mediated binding to chromatin or to scaffold proteins [G. Schlenstedt, FEBS Lett 389, 75 (Jun. 24, 1996)]. Interestingly, unlike the NLS-regulated proteins, ERK2 [M. Costa et al., J Cell Sci 119, 4952 (Dec. 1, 2006)] and other proteins rapidly shuttle between the cytosol and the nucleus upon stimulation. These differences in the mode of shuttling may suggest that the phosphorylation-dependent NTS identified here plays a role in the stimulus-dependent reversible nuclear translocation of these signaling proteins.

Figure 15:
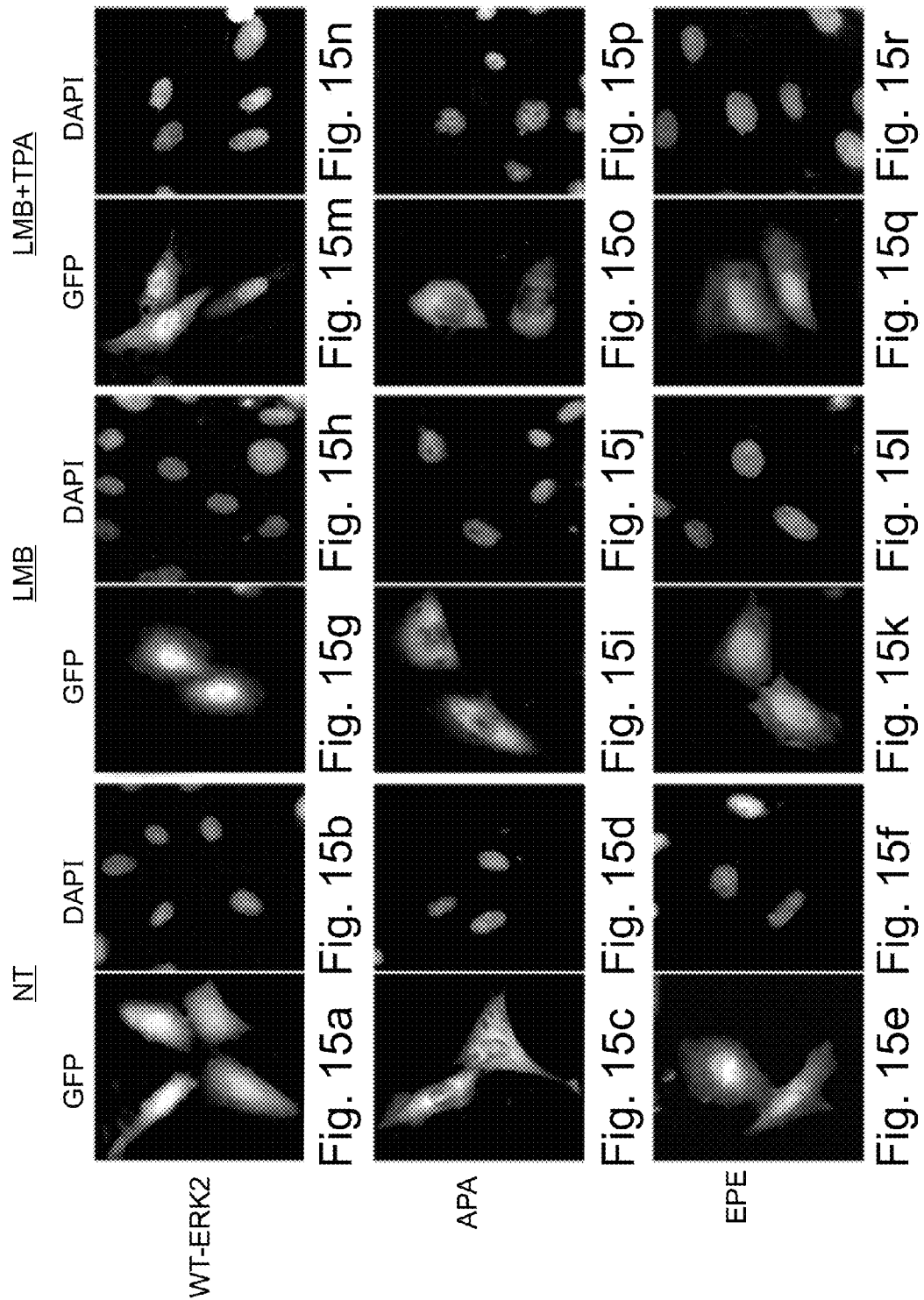
FIGS. 15A-R are photomicrographs illustrating the SPS-phosphorylation regulates nuclear import and not export of ERK2. CHO cells overexpressing WT-ERK, APAERK2 or ePE-ERK2 mutants were starved for 16 hours and treated with OMB (5 ng/ml, 1 hour). LMB+TPA (5 ng/ml LMB for 45 minutes followed by 20 nM TPA for an additional 15 minutes) or left untreated (NT). Subsequently, the cells were fixed, stained with DAPI and visualized by a fluorescent microscope.
Figure 16:
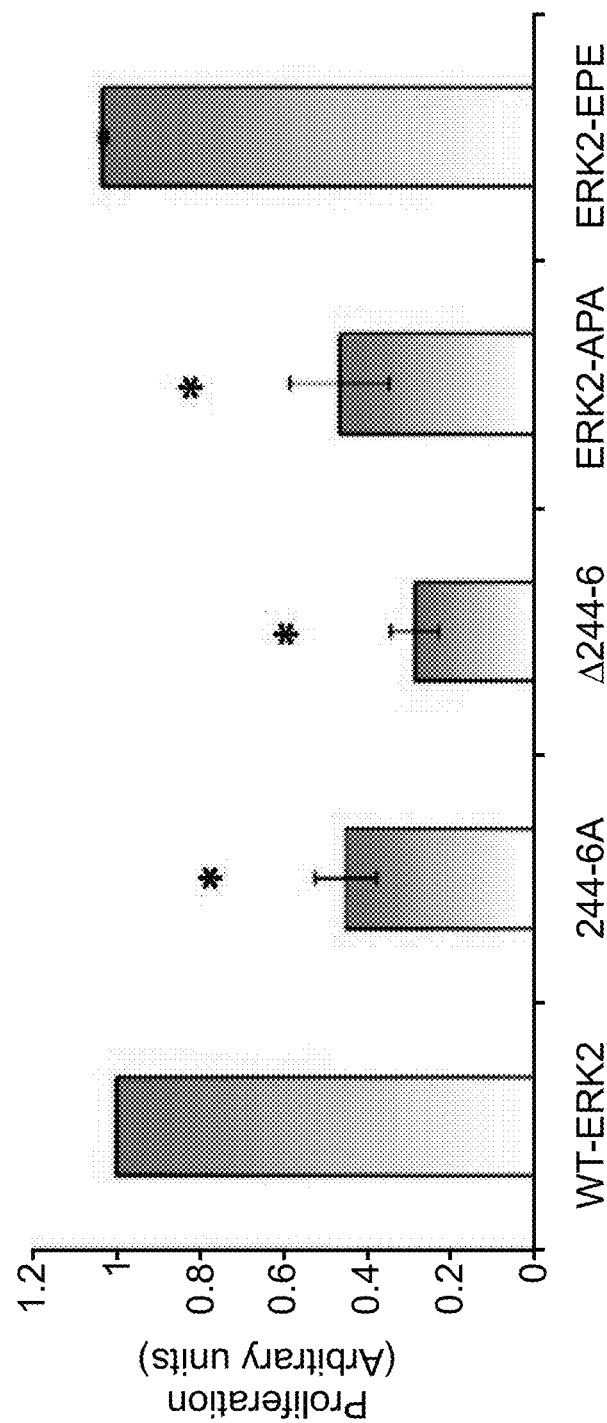
FIG. 16 is a bar graph illustrating that the prevention of SPS phosphorylation inhibits proliferation. COS7 cells overexpressing WT-ERK2, 244-6A-ERK2, ▲244-6-ERK2, APA-ERK2 or EPE-ERK2 were subjected to proliferation assay 72 hours after transfection. The bar graph represent the mean+/−SD (n=3), Student t test was used for statistical analysis (*, $p<0.01$).

The mechanism of action of NTS was extensively studied here, and it was found that the main role of phospho-SPS is to induce import into the nucleus, and not slowing export via the pores or increased anchoring to nuclear proteins (FIGS. 15A-R).

Based on the results obtained here, the present inventors propose a new mechanism for the regulation ERKs' subcellular localization. Thus, in resting cells, ERKs are associated to several cytoplasmic anchors, which is mediated by several protein interaction domains (Chuderland and Seger, 2005, Mol Biotechnol, 29, 57-74). Phosphorylation of their TEY domain by MEKs induces a conformational change, which activates the proteins and induces their detachment from most of the anchors (Wolf et al., 2001, J Biol Chem 276, 24490-24497). The detached proteins are then phosphorylated on their SPS domain by kinases that belong to the ERK cascade, including ERKs themselves (FIGS. 4A-I). This phosphorylation then allows association of the active ERKs to importin-7 (FIGS. 18A-G and FIGS. 19A-C) that carries the ERKs via the nuclear pores into the nucleus. This importin-7-dependent translocation does not require the aid of importin-13 (FIGS. 19A-C) which seems to be required for importin-7 in some, but not all, systems (Gorlich et al., 1997; Jakel and Gorlich, 1998). The actual penetration through the pore requires SPS phosphorylation as well, as it seems to alleviate the strong interaction with NUPs (FIGS. 19A-C) and to allow a proper pore sliding. Once the importin-7-ERK complex reaches the nucleus it is recognized by Ran-GTP (FIGS. 18A-G) and this small GTPase induces dissociation of ERKs from the translocation complex to allow their interaction with nuclear substrates. The present results also indicate that very similar, importin-7 and NTS dependent processes are involved in the nuclear translocation of SMAD3 and MEK1 (FIGS. 11-14).

The scenario above describes the active nuclear translocation of ERKs upon stimulation. However, it was shown that ERKs can translocate into the nucleus via a co-existing passive mechanism as well (Adachi et al., 1999, EMBO, 18, 5347-5358). The present results indicate that the SPS phosphorylation is also required for this type of translocation, as the overexpressed ERKs are accumulated in the nucleus of resting cells in an SPS-dependent manner (FIGS. 5-7 and FIGS. 1M-R). The present inventors also show that SPS domain can also be phosphorylated without a prior TEY phosphorylation (FIGS. 4A-I), and this process could be the mediator of the passive ERKs transport. Although, upon SPS phosphorylation ERK can interact with importin-7 to induce the slow passive nuclear translocation, it is possible that this translocation occurs without the involvement of a transport carrier. In this case the ERKs may directly diffuse to the nuclear pores, and in that case the SPS phosphorylation is solely required for the proper sliding through the pore as mentioned above. Additionally, the present results indicate that dimerization, which was suggested to be involved in the nuclear tranlocation of ERKs (Khokhlatchev et al., 1998, Cell 93, 605-615) is not required for either the active or passive translocation.

Figure 19C:
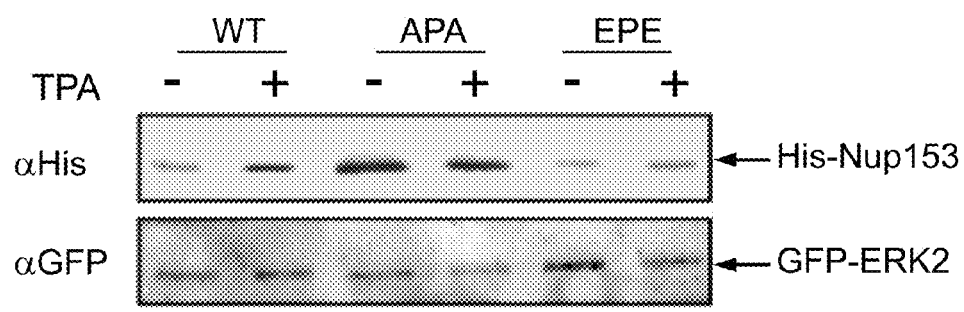

Surprisingly, it was found that unlike the interaction with importins, SPS phopshorylation decreases rather than increases the binding of ERKs to NUP-153 (FIG. 19C). This result may suggest that NUPs binding is mediated by other residues, adjacent to the SPS domain, which might be complementary residues in the SPS-dependent NTS. The phosphorylation of the SPS either reduces this binding affinity to the interacting residues or elevates its $K_{off}$, a process that results a faster release from the NUPs, and allows a smooth sliding through the nuclear pores. Such a binding might have been mediated by hydrophobic regions, which were previously shown important in the binding of NUPs to various proteins (Bayliss et al., 2002, J Biol Chem 277, 50597-50606). Thus, hydrophobic regions in the vicinity of the SPS domain have been implicated in the nuclear translocation of SMAD3 (Xu et al., 2003, J Biol Chem, 278, 42569-42577) and ERK2 (Lee et al., 2004, Mol Cell 14, 43-55), and the present inventors noticed that a proximal hydrophobic region exists also in MEK1 (FIG. 20).

A sequence analysis showed that the NTS is present in the sequences of regulatory nuclear shuttling signaling proteins and might similarly induce their nuclear translocation. One such protein is Cycline-B, in which the region required for translocation contains SPS domain in a Ser-rich region (Walsh et al., 2003). ERK phosphorylation of Ser residues in that region was shown to be important for the mechanism of translocation, and therefore is likely to operate via phosphorylated SPS and support the NTS mechanism identified herein. Other nuclear shuttling, NTS containing proteins are SMAD2 and SMAD4, JNK2, AKT, STAT4, BRCA1, APC, and p53.

In summary, the present inventors have identified a novel, general NTS that participates in nuclear translocation of signaling proteins upon extracellular stimulation. Phosphorylation of the NTS is required for the dynamic and reversible shuttling. The generality and autonomous function of the NTS was validated by overexpression of 2GFP chimera fused to a sequence of 19 amino acids containing the NTS. The mechanism of translocation involves phosphorylation-dependent interaction with importin-7 and release from NUPs, as well as dissociation of the importin-7 complex by Ran-GTP. This mechanism seems to operate, at least in part, in both passive and stimulated nuclear translocation. The NTS-dependent nuclear translocation was identified and characterized for ERK2, SMAD3 and MEK1, but similar sequences in other signaling proteins suggest that the identified NTS may play a general role in the stimulation-dependent translocation of signaling proteins.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a hyperproliferative disease in a subject, the method comprising administering to the subject a therapeutically effective amount of an isolated peptide into the subject, wherein said isolated peptide is less than 20 amino acids and comprises an amino acid sequence at least 70% homologous to the sequence as set forth by:

(SEQ ID NO: 38)
L D Q L N H I L G I L G $X_1$ P $X_1$ Q E D;

wherein $X_1$ is selected from the group consisting of Thr, Asp and Glu, the isolated peptide being capable of preventing ERK nuclear translocation, thereby treating the hyperproliferative disease.

2. The method of claim 1, wherein the hyperproliferative disease is cancer.

3. The method of claim 2, wherein said cancer is selected from the group consisting of melanoma, breast cancer and colorectal cancer.

4. The method of claim 2, wherein said cancer is melanoma.

5. The method of claim 1, wherein the peptide is myristoylated.

* * * * *